(12) United States Patent
Irie et al.

(10) Patent No.: US 7,531,546 B2
(45) Date of Patent: *May 12, 2009

(54) SPIRO-SUBSTITUTED PYRROLO[2,3-D]PYRIMIDINES AS CATHEPSIN INHIBITORS

(75) Inventors: Osamu Irie, Tsukuba (JP); Genji Iwasaki, Tsukuba (JP); Keiichi Masuya, Tsukuba (JP); Takahiro Miyake, Tsukuba (JP); Naoki Teno, Ushiku (JP)

(73) Assignee: Novartis AG, Basel (CH)

( * ) Notice: Subject to any disclaimer, the term of this patent is extended or adjusted under 35 U.S.C. 154(b) by 106 days.

This patent is subject to a terminal disclaimer.

(21) Appl. No.: 10/547,184

(22) PCT Filed: Feb. 27, 2004

(86) PCT No.: PCT/EP2004/001982

§ 371 (c)(1), (2), (4) Date: Jun. 2, 2006

(87) PCT Pub. No.: WO2004/076455

PCT Pub. Date: Sep. 10, 2004

(65) Prior Publication Data

US 2006/0258690 A1    Nov. 16, 2006

(30) Foreign Application Priority Data

Feb. 28, 2003  (GB) .................. 0304640.6

(51) Int. Cl.
*C07D 487/04*   (2006.01)
*A61K 31/519*   (2006.01)
*C07D 519/00*   (2006.01)

(52) U.S. Cl. ............... 514/265.1; 544/230; 544/280

(58) Field of Classification Search ............... 544/230, 544/231; 514/252.15, 265.1
See application file for complete search history.

(56) References Cited

U.S. PATENT DOCUMENTS

2005/0054851 A1*  3/2005  Betschart et al. ............ 544/276

FOREIGN PATENT DOCUMENTS

| WO | WO 01/70743  | 9/2001 |
| WO | WO 03/020721 | 3/2003 |

* cited by examiner

*Primary Examiner*—James O Wilson
*Assistant Examiner*—Susanna Moore
(74) *Attorney, Agent, or Firm*—John Alexander

(57) ABSTRACT

The invention provides compounds of formula (I) or a pharmaceutically acceptable salt or ester thereof formula (I) wherein the symbols have the meaning as defined in the description. Said compounds are inhibitors of cathepsin K and/or cathepsin S and are useful for the treatment of diseases and medical conditions in which cathepsin K and/or cathepsin S is implicated, e.g. various disorders including neuropathic pain, inflammation, rheumatoid arthritis, osteoarthritis, osteoporosis, multiple sclerosis and tumors.

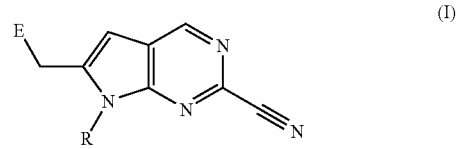

(I)

8 Claims, No Drawings

SPIRO-SUBSTITUTED PYRROLO[2,3-D]PYRIMIDINES AS CATHEPSIN INHIBITORS

This invention relates to inhibitors of cysteine proteases, in particular to pyrrolopyrimide cathepsin K inhibitors or cathepsin S inhibitors or inhibitors with mixed activities and to their pharmaceutical use for the treatment or prophylaxis of diseases or medical conditions in which cathepsin K or cathepsin S is implicated or both are implicated.

Cathepsin K and cathepsin S are members of the family of lysosomal cysteine cathepsin enzymes, comprising e.g. cathepsins B, K, L and S, which are implicated in various disorders including neuropathic pain, inflammation, rheumatoid arthritis, osteoarthritis, osteoporosis, tumors (especially tumor invasion and tumor metastasis), obesity, coronary disease, atherosclerosis (including atherosclerotic plaque rupture and destabilization), autoimmune diseases, multiple sclerosis, respiratory diseases, infectious diseases and immunologically mediated diseases (including transplant rejection). Thus compounds of the invention which are dual inhibitors to cathepsin K and cathepsin S or specific inhibitors to cathepsin S or cathepsin K may be useful in the herein-mentioned diseases.

Accordingly the present invention provides a compound of formula I, or a pharmaceutically acceptable salt or ester thereof

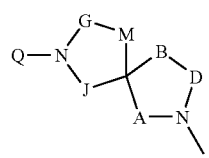

formula I wherein E is a radical of formula a or formula b

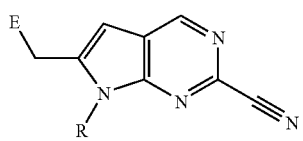

formula a

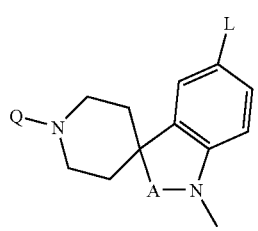

formula b wherein

A is $CH_2$, $CH_2$—$CH_2$ or $C=O$;

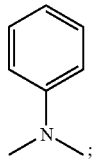

B is $CH_2$, $C=O$ or

D is $CH_2$, or $C=O$;

G is $CH_2$, $CH_2C=O$ or $CH_2$—$CH_2$;

J is $CH_2$, $C=O$ or $CH_2$—$CH_2$;

L is H, $OCH_3$, halo, or lower alkoxy;

M is $CH_2$ or NH;

Q is H, lower alkyl, hydroxy substituted lower alkyl, optionally substituted aryl lower alkyl, lower alkyl sulfonyl, carbocyclic aryl lower alkyl, lower alkoxy-substituted carbocyclic aryl lower alkyl, halo-substituted carbocyclic aryl lower alkyl, N-heterocyclyl-substituted lower alkyl, lower alkoxy substituted carbocyclic aryl, amino carbonyl, cycloalkyl amino carbonyl, N-heterocyclyl substituted lower alkyl carbonyl, halo-substituted carbocyclic aryl lower alkyl, lower alkoxy carbonyl, or lower alkyl carbonyl; and R is lower alkyl, para-chlorophenylethyl, cyclohexylethyl, dimethylbutyl, difluorocyclohexylethyl, cyclopentylethyl or cycloheptylethyl.

In a preferred embodiment of the invention provides a compound of formula I-(i), or a pharmaceutically acceptable salt or ester thereof

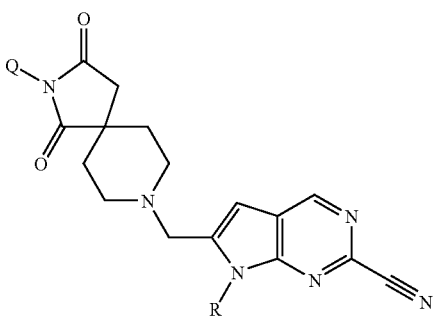

formula I-(i)

wherein

Q-i is H, lower alkyl, hydroxyl-substituted lower alkyl, N-hetercyclyl substituted lower alkyl, mono or di-substituted aryl lower alkyl, lower alkoxy substituted carbocyclic aryl lower alkyl; and R is as defined above.

In another preferred embodiment of the invention provides A compound of formula I-(ii), or a pharmaceutically acceptable salt or ester thereof

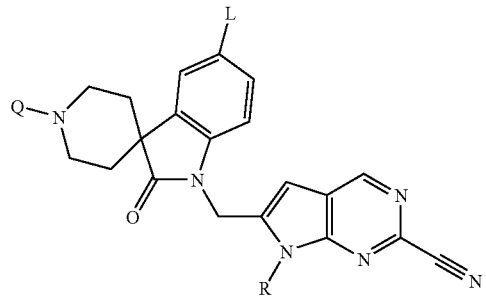

formula I-(ii)

wherein

Q-ii is H, lower alkyl, N-heterocyclyl substituted lower alkyl, halo substituted carbocyclic aryl lower alkyl, lower alkyl carbonyl; and L and R are as defined above.

In a further preferred embodiment of the invention provides a compound of formula I-(iii), or a pharmaceutically acceptable salt or ester thereof

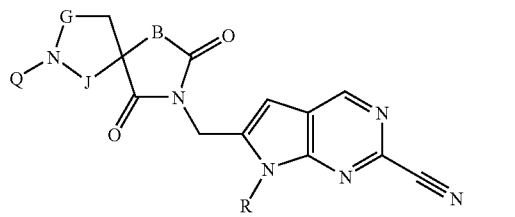

formula I-(iii)

wherein

B-iii is $CH_2$;

G-iii is $CH_2CH_2$;

J-iii is $CH_2CH_2$;

Q-iii is H, cycloalkyl amino carbonyl, amino carbonyl, lower alkoxy substituted carbocyclic aryl, lower alkyl carbonyl, carbocyclic aryl lower alkyl or N-heterocyclyl substituted lower alkyl carbonyl; and R is as defined above.

In a further preferred embodiment of the invention provides a compound of formula I, formula I-(i), formula I-(ii) or formula I-(iii), wherein R is R1=lower alkyl.

In a further preferred embodiment of the invention provides a compound of formula I, formula I-(i), formula I-(ii) or formula I-(iii), wherein R is R5=2,2-dimethyl-propyl.

In a further preferred embodiment of the invention provides a compound of formula I, formula I-(i), formula I-(ii) or formula I-(iii), wherein R is R6=3,3-dimethyl-byutyl.

In a further preferred embodiment of the invention provides a compound of formula I, formula I-(i), formula I-(ii) or formula I-(iii), wherein R is R2=para-chlorophenylethyl, cyclohexylethyl, dimethylbutyl, difluorocyclohexylethyl, cyclopentylethyl or cycloheptylethyl.

In a further preferred embodiment of the invention provides a compound of formula I-(iv), or a pharmaceutically acceptable salt or ester thereof

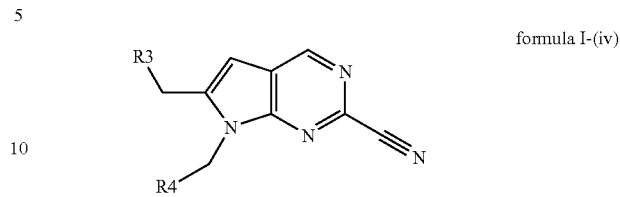

formula I-(iv)

wherein

R3 is (8-lower alkyl-carbonyl)-2,8-diaza-spiro[4.5]dec-2-ylmethyl, (8-lower alkyl-sulfonyl)-2,8-diaza-spiro[4.5]dec-2-ylmethyl, (8-aryl-lower alkyl)-2,8-diaza-spiro[4.5]dec-2-ylmethyl,

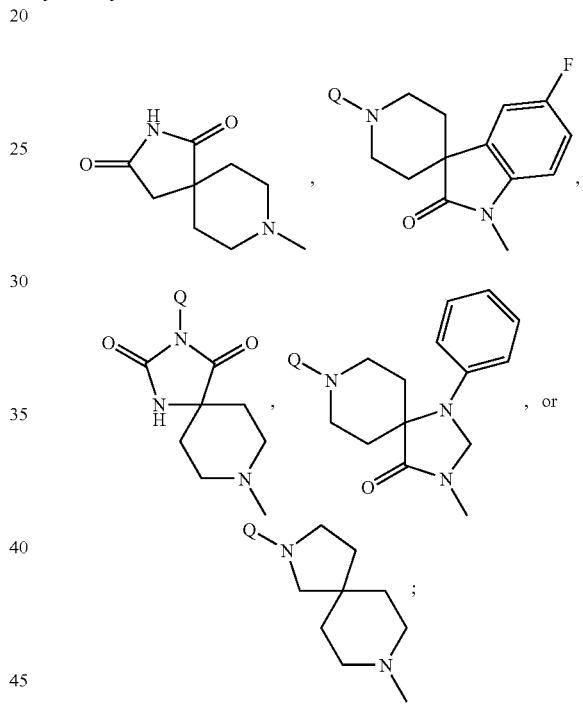

R4 is para-chlorophenylmethyl, cyclohexylmethyl, dimethylpropyl, difluorocyclohexylmethyl, cyclopentylmethyl or cycloheptylmethyl; and Q is as defined above.

The present invention further provides processes for the preparation of compounds of formula I and their salts and esters, comprising the step of coupling a compound of formula II

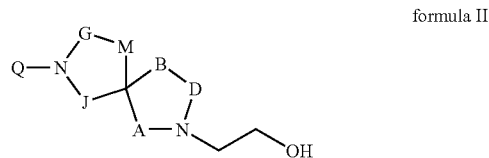

formula II wherein Q, G, J, M, A, B, D are as defined above, with a compound of formula III $$\text{X—CH}_2 \underset{R}{\overset{}{\diagup}} \text{(formula III)}$$

formula III wherein X is a halo and R is defined above, and recovering the resulting compound in free base, or in a pharmaceutically acceptable salt or ester thereof.

The above coupling procedure may be carried out in solution e.g. DMF solution in the presence of $K_2CO_3$, for instance at room temperature with stirring e.g. for about 12 hours. As appropriate protecting groups may be used to protect reactive functional groups during the coupling procedure and may be removed after the coupling procedure, for instance as hereinafter described in the Examples.

Working up the reaction mixtures and purification of the compounds thus obtained may be carried out in accordance to known procedures or according to the Examples.

Above and elsewhere in the present description the following terms have the following meanings.

Halo or halogen denote I, Br, Cl or F.

The term "lower" referred to above and hereinafter in connection with organic radicals or compounds respectively defines such as branched or unbranched with up to and including 6 carbon atoms.

A "lower alkyl" group is branched or unbranched and contains 1 to 6 carbon atoms. Lower alkyl represents, for example, methyl, ethyl, propyl, butyl, isopropyl isobutyl, tertiary butyl or neopentyl(2,2-dimethylpropyl).

"Halo-substituted lower alkyl" is C1-C7 lower alkyl substituted by up to 6 halo atoms, preferably mono, di or tri-substituted lower alkyl.

A "lower alkoxy" group is branched or unbranched and contains 1 to 6 carbon atoms, preferably 1-4 carbon atoms. Lower alkoxy represents for example methoxy, ethoxy, propoxy, butoxy, isopropoxy, isobutoxy or tertiary butoxy.

"Aryl" represents a phenyl or naphthyl radical. Preferably a "carbocyclic aryl" consisting solely of carbon and hydrogen atoms optionally substituted, mono-, di- or tri-substituted by one, two or three radicals selected from lower alkyl, lower alkoxy, hydroxy, halogen, Preferred as carbocyclic aryl is phenyl or phenyl optionally substituted, for instance, as described in the examples, e.g. mono-, di- or tri-substituted by halogen, lower alkyl, lower or alkoxy.

"Cycloalkyl" represents a saturated cyclic hydrocarbon optionally substituted by lower alkyl which contains 3 to 10 ring carbons and is advantageously cyclopropyl, cyclopentyl, cyclohexyl or optionally substituted by lower alkyl.

"N-heterocyclyl" represents a saturated, partially unsaturated or aromatic nitrogen containing heterocyclic moiety attached via a nitrogen atom having from 3 to 8 ring atoms, optionally containing a further O heteroatom optionally substituted by a lower alkyl or lower alkyl carbonyl.

"Lower alkyl carbonyl" refers to a radical of the formula —C(O)$R_a$ where $R_a$ is a lower alkyl radical defined above, for example, acetyl, ethylcarbonyl, or n-propylcarbonyl.

Compounds of the invention are either obtained in the free form, or as a salt thereof if salt forming groups are present. Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as (C1-C4)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as (C1-C4)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

If one or more other functional groups, for example carboxy, hydroxy, amino, or mercapto, are or need to be protected in a compound of formulae I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The starting compounds of formula II and formula III may be produced as described in the Examples.

The compounds of the invention exhibit valuable pharmacological properties in mammals and are therefore useful as pharmaceuticals. They are particularly useful as inhibitors of cathepsin K or cathepsin S or both.

The cathepsin K inhibitory effects of the compound of the invention can be demonstrated in vitro by measuring the inhibition of e.g. recombinant human cathepsin K.

The in vitro assay is carried out as follows:

The assay is performed in 96 well microtiter plates at ambient temperature using recombinant human cathepsin K. Inhibition of cathepsin K is assayed at a constant enzyme (0.16 nM) and substrate concentration (54 mM Z-Phe-Arg-AMCA—Peptide Institute Inc. Osaka, Japan) in 100 mM sodium phosphate buffer, pH 7.0, containing 2 mM dithiothreitol, 20 mM Tween 80 and 1 mM EDTA. Cathepsin K is preincubated with the inhibitors for 30 min, and the reaction is initiated by the addition of substrate. After 30 min incubation the reaction is stopped by the addition of E-64 (2 mM), and fluorescence intensity is read on a multi-well plate reader at excitation and emission wavelengths of 360 and 460 nm, respectively.

Compounds of the Invention typically have $IC_{50}$s for inhibition of human cathepsin K of less than about 100 nM down to about 1 nM or less, preferably of about 5 nM or less, e.g. about 0.2 nM. Example 3-0 has a $IC_{50}$ in the above described assay of about 0.16 nM. Preferred are compounds as defined above with R=R1, e.g. compounds of examples 1 to 4 with R=R1, which have cathepsin K inhibitory effects. More preferred are compounds as defined above with R=R5, most preferred Example 3-0.

The cathepsin S inhibitory effects of the compound of the invention can be demonstrated in vitro by measuring the inhibition of e.g. recombinant human cathepsin S.

The in vitro assay is carried out in clear, flat-bottomed, 96-well microtiter plates (Greiner GmbH, Germany) at ambient temperature using recombinant human cathepsin S. Inhibition of human cathepsin S is assayed at a constant enzyme and various substrate concentrations (substrate is Z-Leu-Leu-4-methylcoumaryl-7-amide (Bachem (Switzerland)) in 100 parts 0.2M sodium phosphate, pH 7.0, containing 2 mM EDTA, 2 parts 1% Triton X-100, 10 parts 20 mM dithiothreitol (DTT) and 58 parts distilled water. The assay is started by adding the enzyme solution (13 times higher concentration of final concentration of recombinant human Cathepsin S) to the reaction mixture containing various concentrations of the corresponding substrate and the compound. Substrate concentrations between 3.4 and 17 µM are used. The recombinant human Cathepsin S is used at a final concentration of 0.04 nM. Test compounds are used at concentrations between 0.4 and 2 times the determined IC50 of the compound at the enzyme. The relative fluorescence is continuously measured for 30 minutes and the initial velocity is obtained from each progress curve. The inhibition patterns and the $K_i$ values are determined by Dixon plot analysis.

Compounds of the Invention typically have $IC_{50}$s for inhibition of human cathepsin S of less than about 100 nM down to about 1 nM or less, preferably of about 5 nM or less. Preferred compounds are compounds as defined above with R=R2. E.g. example 4-8 has a $IC_{50}$ in the above described assay of about 9 nM.

Compounds of the Invention which have dual inhibitory effects, i.e. inhibitory effects in the cathepsin K and the cathepsin S assay as described above typically have $IC_{50}$s for inhibition of human cathepsin S and of cathepsin K of less than about 100 nM in both assays, down to about 1 nM or less in both assays, preferably of about 5 nM or less. Preferred compounds with a dual inhibitory effect are compounds as defined above with R=R6. E.g. example 4-3 with an $IC_{50}$ on human cathepsin K of 8 nM and on human cathepsin S of 6 nM. Or example 4-9 with an $IC_{50}$ on human cathepsin K of 16 nM and on human cathepsin S of 10 nM.

In view of their activity as inhibitors of cathepsin K and/or cathepsin S, compounds of the invention are particularly useful in mammals as agents for treatment and prophylaxis of diseases and medical conditions involving elevated levels of cathepsin K and/or cathepsin S. Such diseases include diseases involving infection by organisms such as *pneumocystis carinii, trypsanoma cruzi, trypsanoma brucei, crithidia fusiculata*, as well as parasitic diseases such as schistosomiasis and malaria, tumours (tumour invasion and tumour metastasis), and other diseases such as metachromatic leukodystrophy, muscular dystrophy, amytrophy, neuropathic pain, e.g. chronic neuropathic pain, exemplified by conditions such as diabetic neuropathy, postherpetic neuralgia, trigeminal neuralgia, painful diabetic polyneuropathy, post-stroke pain (central pain), postamputation pain, myolopathic or radiculopathic pain (e.g. spinal stenosis, arachnoiditis, root sleeve fibrosis), atypical facial pain and causalgia-like syndromes (complex regional pain syndromes), autoimmune disorders, including, but not limited to juvenile onset diabetes and multiple sclerosis, allergic disorders, including, but not limited to, asthma, and allogeneic immune responses, including, but not limited to, organ transplant rejection.

In particular, cathepsin K has been implicated in diseases of excessive bone loss, and thus the Compounds of the Invention may be used for treatment and prophylaxis of such diseases, including osteoporosis, osteoporosis of various genesis (e.g. juvenile, menopausal, post-menopausal, post-traumatic, caused by old age or by cortico-steroid therapy or inactivity), gingival diseases such as gingivitis and periodontitis, Paget's disease, hypercalcemia of malignancy, e.g. tumour-induced hypercalcemia and metabolic bone disease. Also the Compounds of the Invention may be use for treatment or prophylaxis of diseases of excessive cartilage or matrix degradation, including osteoarthritis and rheumatoid arthritis as well as certain neoplastic diseases involving expression of high levels of proteolytic enzymes and matrix degradation. Preferably cathepsin K inhibitors are used in the treatment of osteoporosis and osteoarthritis.

In particular, cathepsin S has been implicated in the treatment and also in the prevention of neuropathic pain, e.g. chronic neuropathic pain, exemplified by conditions such as diabetic neuropathy, postherpetic neuralgia, trigeminal neuralgia, painful diabetic polyneuropathy, post-stroke pain (central pain), postamputation pain, myolopathic or radiculopathic pain (e.g. spinal stenosis, arachnoiditis, root sleeve fibrosis), atypical facial pain and causalgia-like syndromes (complex regional pain syndromes), osteoarthritis and rheumatoid arthritis, autoimmune disorders, including, but not limited to juvenile onset diabetes and multiple sclerosis, allergic disorders, including, but not limited to, asthma, and allogeneic immune responses, including, but not limited to, organ transplant rejection. Preferably cathepsin S inhibitors are used in the treatment of neuropathic pain, multiple sclerosis, osteoarthritis and rheumatoid arthritis.

Dual inhibitors may thus be implicated in diseases of where both cathepsins play a role, e.g. neuropathic pain, inflammation, rheumatoid arthritis, osteoarthritis, osteoporosis, tumors (especially tumor invasion and tumor metastasis), obesity, coronary disease, atherosclerosis (including atherosclerotic plaque rupture and destabilization), autoimmune diseases, multiple sclerosis, respiratory diseases, infectious diseases and immunologically mediated diseases (including transplant rejection), preferably neuropathic pain, osteoporosis, rheumatoid arthritis, and osteoarthritis.

Beneficial effects are evaluated in in vitro and in vivo pharmacological tests generally known in the art, and as illustrated herein. The above cited properties are demonstrable in vitro and in vivo tests, using advantageously mammals, e.g. rats, mice, dogs, rabbits, monkeys or isolated organs and tissues, as well as mammalian enzyme preparations, either natural or prepared by e.g. recombinant technology. Compounds of the Invention can be applied in vitro in the form of solutions, e.g. preferably aqueous solutions or suspensions, and in vivo either enterally or parenterally, advantageously orally, e.g. as a suspension or in aqueous solution, or as a solid capsule or tablet formulation. The dosage in vitro may range between about $10^{-5}$ molar and $10^{-9}$ molar concentrations. The dosage in vivo may range, depending on the route of administration, between about 0.1 and 100 mg/kg.

The efficacy of the Compounds of the Invention for the treatment of osteoporosis can be determined using the In vivo animal model "OVX cynomolgus monkey". This model is well known in the art and is a common model to validate an osteoporosis compound (see e.g. Jerome C P, Peterson P E (2001) Bone; 29 (1):1-6).

The efficacy of the Compounds of the Invention for the treatment of chronic inflammatory or neuropathic pain can be determined using the following In vivo animal models:

Chronic Inflammatory Pain Model:

The Complete Freund's Adjuvant-induced mechanical hyperalgesia may be used as a model of chronic inflammatory pain (Stein, C. et al. Pharmacol. Biochem. Behav. (1988) 31: 445-451). In this model, typically a male Sprague-Dawley or Wistar rat (200-250 g) receives an intraplantar injection of 25 µl complete Freund's adjuvant into one hind paw. A marked inflammation occurs in this hind paw. Drugs are generally administered for evaluation of efficacy, 24 hours after the inflammatory insult, when mechanical hyperalgesia is considered fully established.

Chronic Neuropathic Pain Models:

Two animal models of chronic neuropathic pain may be used that involve some form of peripheral nerve damage. In the Seltzer model (Seltier et al. (1990) Pain 43: 205-218) rats are anaesthetised and a small incision made mid-way up one thigh (usually the left) to expose the sciatic nerve. The nerve is carefully cleared of surrounding connective tissues at a site near the trochanter just distal to the point at which the posterior biceps semitendinosus nerve branches off the common sciatic nerve. A 7-0 silk suture is inserted into the nerve with a ⅜ curved, reversed-cutting mini-needle, and tightly ligated so that the dorsal ⅓ to ½ of the nerve thickness is held within the ligature. The muscle and skin are closed with sutures and clips and the wound dusted with antibiotic powder. In sham animals the sciatic nerve is exposed but not ligated and the wound closed as in nonsham animals.

In the Chronic Constriction Injury (CCI) model (Bennett, G. J. and Xie, Y. K. Pain (1988) 33: 87-107) rats are anaesthetised and a small incision is made mid-way up one thigh (usually the left) to expose the sciatic nerve. The nerve is cleared of surrounding connective tissue and four ligatures of 4/0 chromic gut are tied loosely around the nerve with approximately 1 mm between each, so that the ligatures just barely constrict the surface of the nerve. The wound is closed with sutures and clips as described above. In sham animals the sciatic nerve is exposed but not ligated and the wound closed as in nonsham animals.

In contrast to the Seltzer and CCI models, the Chung model involves ligation of the spinal nerve. (Kim, S. O. and Chung, J. M. Pain (1992): 50:355-363). In this model, rats are anesthetized and placed into a prone position and an incision is made to the left of the spine at the L4-S2 level. A deep dissection through the paraspinal muscles and separation of the muscles from the spinal processes at the L4-S2 level will reveal part of the sciatic nerve as it branches to form the L4, L5 and L6 spinal nerves. The L6 transverse process is carefully removed with a small rongeur enabling visualisation of these spinal nerves. The L5 spinal nerve is isolated and tightly ligated with 7-0 silk suture. The wound is closed with a single muscle suture (6-0 silk) and one or two skin closure clips and dusted with antibiotic powder. In sham animals the L5 nerve is exposed as before but not ligated and the wound closed as before.

Behavioral Index

In all chronic pain models (inflammatory and neuropathic) mechanical hyperalgesia is assessed by measuring paw withdrawal thresholds of both hindpaws to an increasing pressure stimulus using an Analgesymeter (Ugo-Basile, Milan). Mechanical allodynia is assessed by measuring withdrawal thresholds to non-noxious mechanical stimuli applied with von Frey hairs to the plantar surface of both hindpaws. Thermal hyperalgesia is assessed by measuring withdrawal latencies to a noxious thermal stimulus applied to the underside of each hindpaw. With all models, mechanical hyperalgesia and allodynia and thermal hyperalgesia develop within 1-3 days following surgery and persist for at least 50 days. For the assays described herein, drugs may be applied before and after surgery to assess their effect on the development of hyperalgesia, particularly approximately 14 days following surgery, to determine their ability to reverse established hyperalgesia.

The percentage reversal of hyperalgesia is calculated as follows:

$$\% \text{ reversal} = \frac{\text{postdose threshold} - \text{predose threshold}}{\text{naive threshold} - \text{predose threshold}} \times 100$$

In the experiments disclosed herein, Wistar rats (male) are employed in the pain models described above. Rats weigh approximately 120-140 grams at the time of surgery. All surgery is performed under enflurane/$O_2$ inhalation anaesthesia. In all cases the wound is closed after the procedure and the animal allowed to recover. In all pain models employed, after a few days in all but the sham operated animals, a marked mechanical and thermal hyperalgesia and allodynia develops in which there is a lowering of pain threshold and an enhanced reflex withdrawal response of the hind-paw to touch, pressure or thermal stimuli. After surgery the animals also exhibit characteristic changes to the affected paw. In the majority of animals the toes of the affected hind paw are held together and the foot turned slightly to one side; in some rats the toes are also curled under. The gait of the ligated rats varies, but limping is uncommon. Some rats are seen to raise the affected hind paw from the cage floor and to demonstrate an unusual rigid extension of the hind limb when held. The rats tend to be very sensitive to touch and may vocalise. Otherwise the general health an condition of the rats is good.

Compounds of the invention, are also indicated for preventing or treating coronary disease, atherosclerosis (including atherosclerotic plaque rupture and destabilization) (see e.g. Cathepsin F and S block HDL3-induced cholesterol efflux from macrophage cells, Lindstedt et al., 2003, Biochemical and Biophysical research communications 312: 1019-1024), autoimmune diseases, respiratory diseases and immunologically mediated diseases (including transplant rejection).

The antiarthritic efficacy of the compounds of the invention for the treatment of rheumatoid arthritis can be determined using models such as or similar to the rat model of adjuvant arthritis, as described previously (R. E. Esser, et. al. J. Rheumatology, 1993, 20, 1176.)

The efficacy of the compounds of the invention for the treatment of osteoarthritis can be determined using models such as or similar to the rabbit partial lateral meniscectomy model, as described previously (Colombo et al. Arth. Rheum. 1993 26, 875-886). The efficacy of the compounds in the model can be quantified using histological scoring methods, as described previously (O'Byrne et al. Inflamm Res 1995, 44, S117-S118).

The efficacy of the compounds of the invention for the treatment of osteoporosis can be determined using an animal model such as the ovariectomised rat or other similar species, e.g. rabbit or monkey, in which test compounds are administered to the animal and the presence of markers of bone resorption are measured in urine or serum (e.g. as described in Osteoporos Int (1997) 7:539-543).

Accordingly In Further Aspects The Invention Provides:

A compound of the invention for use as a pharmaceutical; a pharmaceutical composition comprising a compound of the invention as an active ingredient; a method of treating a patient suffering from or susceptible to a disease or medical condition in which cathepsin K and/or cathepsin S is implicated, comprising administering an effective amount of a compound of the invention to the patient, and the use of a compound of the invention for the preparation of a medicament for therapeutic or prophylactic treatment of a disease or medical condition in which cathepsin K and/or cathepsin S is implicated.

The present invention relates to methods of using compounds of the invention and their pharmaceutically acceptable salts, or pharmaceutical compositions thereof, in mammals for inhibiting cathepsin K and/or cathepsin S, and for the treatment of cathepsin K and/or cathepsin S dependent conditions, such as the cathepsin K and/or cathepsin S dependent conditions, described herein, e.g. inflammation, neuropathic pain, osteoporosis, rheumatoid arthritis and osteoarthritis.

In a particular embodiment of the invention, the present invention relates to a method of selectively inhibiting cathepsin K activity in a mammal which comprises administering to a mammal in need thereof an effective cathepsin K inhibiting amount of a compound of the invention.

More specifically such relates to a method of treating osteoporosis, rheumatoid arthritis, osteoarthritis, and inflammation (and other diseases as identified above) in mammals comprises administering to a mammal in need thereof a correspondingly effective amount of a compound of the invention.

In a particular embodiment of the invention, the present invention relates to a method of selectively inhibiting cathepsin S activity in a mammal which comprises administering to a mammal in need thereof an effective cathepsin S inhibiting amount of a compound of the invention.

More specifically such relates to a method of treating neuropathic pain (and other diseases as identified above) in mammals comprises administering to a mammal in need thereof a correspondingly effective amount of a compound of the invention.

In a particular embodiment of the invention, the present invention relates to a method of inhibiting cathepsin K and cathepsin S activity in a mammal which comprises administering to a mammal in need thereof an effective cathepsin K and cathepsin S inhibiting amount of a compound of the invention.

More specifically such relates to a method of treating neuropathic pain, osteoporosis, rheumatoid arthritis, osteoarthritis, and inflammation (and other diseases as identified above) in mammals comprises administering to a mammal in need thereof a correspondingly effective amount of a compound of the invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20-133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLES

Example 1

Example 1-0

Preparation of 7-(2,2-Dimethyl-propyl)-6-[2-(2-hydroxy-ethyl)-1,3-dioxo-2,8-diaza-spiro[4.5]dec-8-ylmethyl]-7H-pyrrolo[2,3-d]pyrimidine-2-carbonitrile

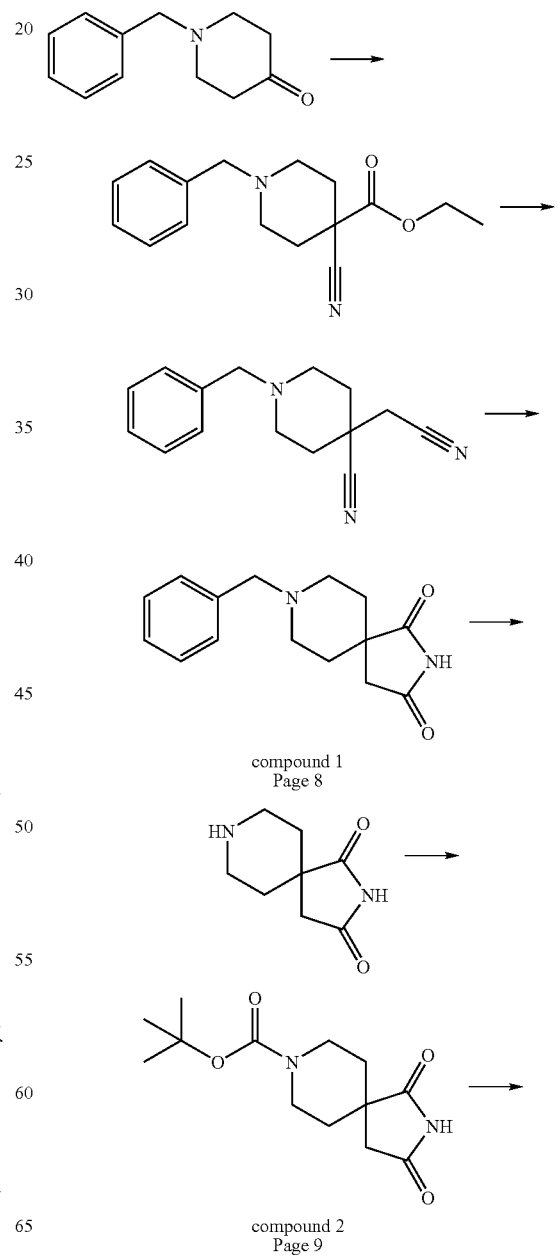

compound 1
Page 8 compound 2
Page 9

-continued

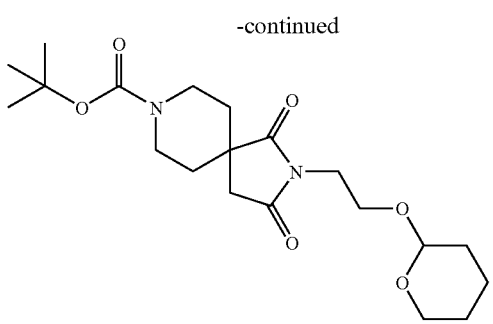

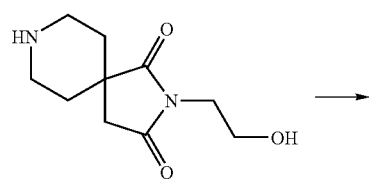

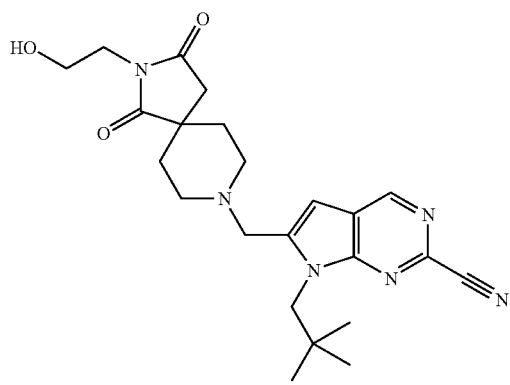

A. Preparation of 8-Benzyl-2,8-diaza-spiro[4.5]decane-1,3-dione

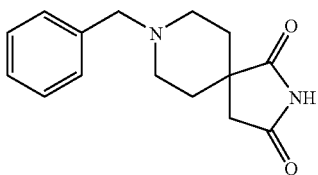

To a solution of 1-benzyl-piperidin-4-one (75.1 g, 0.40 mol) in toluene (400 ml), cyano-acetic acid ethyl ester (50.6 ml, 0.48 mol) and acetic acid (18.2 ml, 0.32 mol) are added at ambient temperature. The reaction mixture is refluxed for 4 h, quenched with ice-water and extracted with diethyl ether. The combined extracts are washed with $H_2O$, brine and dried over sodium sulphate to give (1-benzyl-piperidin-4-ylidene)-cyano-acetic acid ethyl ester in quantitative yield.

Rf=0.53 (n-hexane:AcOEt=1:1).

$^1$H-NMR (400 MHz, CDCl$_3$) δ: 1.30-1.37 (m, 3H), 2.58 (dd, 2H), 2.64 (dd, 2H), 2.79 (dd, 2H), 3.15 (dd, 2H), 3.55 (s, 2H), 4.23-4.32 (m, 2H), 7.21-7.36 (m, 5H).

To a solution of (1-benzyl-piperidin-4-ylidene)-cyano-acetic acid ethyl ester (112.9 g, 0.40 mol) in EtOH (500 ml) and $H_2O$ (100 ml), potassium cyanide (64.6 g, 0.99 mol) is added at ambient temperature. The reaction mixture is stirred at 65 C.° for 24 h. After removal of EtOH, $H_2O$ is added to the residue. The waster phase is extracted with diethyl ether. The combined extracts are washed with $H_2O$ and brine, dried over sodium sulfate and evaporated down to give 77.7 g of 1-benzyl-4-cyanomethyl-piperidine-4-carbonitrile.

Rf=0.38 (n-hexane:AcOEt=1:1).

$^1$H-NMR (400 MHz, CDCl$_3$) δ: 1.76-1.81 (m, 2H), 2.10-2.05 (m, 2H), 2.23-2.39 (m, 2H), 2.69 (s, 2H), 2.90-2.94 (m, 2H), 3.56 (s, 2H), 7.21-7.38 (m, 5H).

Acetic acid (56.8 ml) and sulfuric acid (11.8 ml) are added to 1-benzyl-4-cyanomethyl-piperidine-4-carbonitrile (27.2 g, 0.114 mmol) at ambient temperature. The reaction mixture is stirred at 125 C.° for 1 h, cooled down to the room temperature and added to saturated NaOH aq. to adjust to pH 6.0. The mixture is extracted with dichloromethane. The combined extracts are washed with $H_2O$ and brine, dried over sodium sulfate and evaporated down to give 8-benzyl-2,8-diaza-spiro[4.5]decane-1,3-dione (three steps yield: 81.8%).

Rf=0.40 (CH$_2$Cl$_2$:MeOH=10:1).

$^1$H-NMR (400 MHz, CDCl$_3$) δ: 1.52-1.57 (m, 2H), 2.02-2.17 (m, 4H), 2.59 (s, 2H), 2.86-2.90 (m, 2H), 3.52 (s, 2H), 7.21-7.28 (m, 2H), 7.30-7.37 (m, 3H), 7.92 (brs, 1H).

B. Preparation of 1,3-Dioxo-2,8-diaza-spiro[4.5]decane-8-carboxylic acid tert-butyl ester

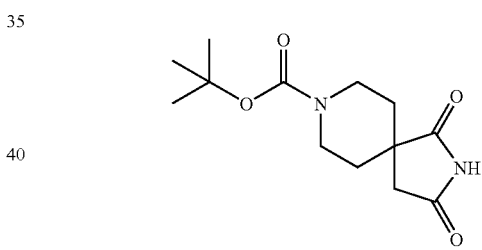

To 8-benzyl-2,8-diaza-spiro[4.5]decane-1,3-dione (28.3 g, 0.11 mol) and Pd(OH)$_2$ (8.5 g) in 2 l of flask, EtOH (438 ml) and acetic acid (5.5 ml) are added at ambient temperature. The reaction mixture is stirred under H$_2$ at room temperature for 15 h. The catalysts are removed by filtration and EtOH is evaporated down to give 2,8-diaza-spiro[4.5]decane-1,3-dione in quantitative yield. To a suspension of 2,8-diaza-spiro[4.5]decane-1,3-dione (4.2 g, 25.2 mmol) in dichloromethane (60 ml), 1N NaOH (26 ml, 26 mmol) and di-t-butyldicarbonate (6.1 g, 27.7 mmol) in dichloromethane (20 ml) are added at ambient temperature. The reaction mixture is stirred for 15 h. 10% Citric acid is added to the reaction mixture and the pH of the mixture is adjusted to 5. The combined extracts are washed with brine, dried over magnesium sulfate and concentrated under vacuum to give solid product, which filtrated with diethyl ether.

Yield: 51%

Rf=0.25 (n-hexane:ethyl acetate=1:1).

$^1$H-NMR (400 MHz, CDCl$_3$) δ: 1.47 (s, 9H), 1.55-1.70 (m, 2H), 1.95-2.05 (m, 2H), 2.62 (s, 2H), 2.96-3.02 (m, 2H), 4.02-4.04 (m, 2H), 8.14 (brs, 1H).

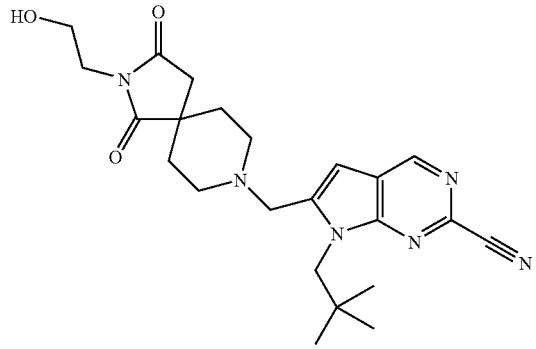

Preparation of 1,3-dioxo-2-[2-(tetrahydro-pyran-2-yloxy)-ethyl]-2,8-diaza-spiro[4.5]decane-8-carboxylic acid tert-butyl ester To a suspension of 1,3-dioxo-2,8-diaza-spiro[4.5]decane-8-carboxylic acid tert-butyl ester (1.0 g, 3.7 mmol) in DMF (12 ml), 2-(2-bromoethoxy)-tetrahydro-2H-pyrane (0.62 ml, 4.1 mmol) and potassium carbonate (0.62 g, 4.5 mmol) are added at ambient temperature and the mixture is stirred for overnight at room temperature. The reaction mixture is quenched with water and extracted with ethyl acetate. The combined extracts are washed with brine and dried over sodium sulfate, filtrated. The solvent is evaporated down to give 1.6 g of crude 1,3-dioxo-2-[2-(tetrahydro-pyran-2-yloxy)-ethyl]-2,8-diaza-spiro[4.5]decane-8-carboxylic acid tert-butyl ester.

Preparation of 2-(2-hydroxy-ethyl)-2,8-diaza-spiro[4.5]decane-1,3-dione. hydrochloride To a solution of crude 1,3-dioxo-2-[2-(tetrahydro-pyran-2-yloxy)-ethyl]-2,8-diaza-spiro[4.5]decane-8-carboxylic acid tert-butyl ester (1.6 g) in ethyl acetate (1 ml), EtOH (1.0 ml) and 4N HCl/ethyl acetate (4 ml) are added at room temperature. The reaction mixture is stirred for overnight at room temperature. The solvent is removed by evaporation to give 1.06 g of crude 2-(2-hydroxy-ethyl)-2,8-diaza-spiro[4.5]decane-1,3-dione. hydrochloride.

Preparation of 7-(2,2-Dimethyl-propyl)-6-[2-(2-hydroxy-ethyl)-1,3-dioxo-2,8-diaza-spiro[4.5]dec-8-ylmethyl]-7H-pyrrolo[2,3d]pyrimidine-2-carbonitrile 6-Bromomethyl-7-(2,2-dimethyl-propyl)-7H-pyrrolo[2,3-d]pyrimidine-2-carbonitrile (1.3 g, 4.25 mmol) and crude 2-(2-hydroxy-ethyl)-2,8-diaza-spiro[4.5]decane-1,3-dione. hydrochloride (1.1 g, 4.25 mmol) are dissolved in DMF (14 ml) and potassium carbonate (1.8 g, 12.8 mmol) is added to the solution. The reaction mixture is stirred at room temperature for 12 h and quenched with H$_2$O and extracted with ethyl acetate. The combined extracts are washed with brine, dried over magnesium sulfate and evaporated down. The crude product is purified by reverse phase HPLC and fraction are collected and evaporated down. Saturated sodium bicarbonate is added and neutralized and the water phase is extracted with ethyl acetate. The combined extracts are washed with brine, dried over magnesium sulfate and evaporated down to give 0.5 g of desired product in 27% yield.

Rf=0.10 (n-hexane:ethyl acetate=1:1).

$^1$H-NMR (400 MHz, CDCl$_3$) δ: 1.01 (s, 9H), 1.52-1.60 (m, 2H), 2.08-2.14 (m, 4H), 2.60 (s, 2H), 2.84-2.88 (m, 2H), 3.71-3.78 (m, 4H), 3.81 (s, 2H), 4.34 (s, 2H), 6.58 (s, 1H), 8.89 (s, 1H).

By repeating the procedures described above using appropriate starting materials and conditions the following compounds of formula I are obtained as identified below in Table 1.

Formula I-(i)

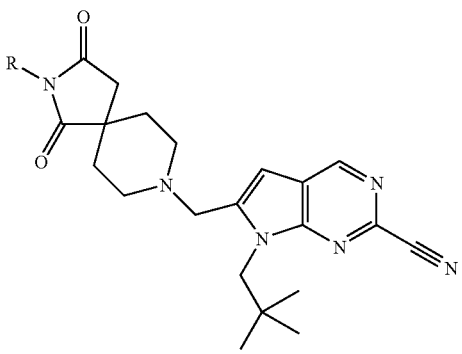

TABLE 1

| Example | Rx | Yield (%) | Rf(Solvent) | NMR(400 MHz, δ) |
|---|---|---|---|---|
| 1-1 | H | 43 | 0.48 (EtOAc only) | (CDCl$_3$): 1.03 (s, 9H), 1.50-1.57 (m, 2H), 2.10-2.25 (m, 4H), 2.62 (s, 2H), 2.84-2.95 (m, 2H), 3.83 (s, 2H), 4.36 (s, 2H), 6.60 (s, 1H), 7.74 (brs, 1H), 8.91 (s, 1H) |

TABLE 1-continued

| Example | Rx | Yield (%) | Rf(Solvent) | NMR(400 MHz, δ) |
|---|---|---|---|---|
| 1-2 | (isobutyl-like, CH(CH3)- branch) | 40 | 0.20 (n-hexane:AcOEt = 1:1) | (CDCl$_3$): 1.01 (s, 9H), 1.48-1.52 (m, 2H), 2.11-2.16 (m, 4H), 2.55 (s, 2H), 2.84-2.87 (m, 2H), 3.00 (s, 3H), 3.81 (s, 2H), 4.35 (s, 2H), 6.58 (s, 1H), 8.89 (s, 1H) |
| 1-3 | n-propyl | 30 | 0.50 (n-hexane:AcOEt = 1:1) | (CDCl$_3$):): 0.88 (t, 3H), 1.01 (s, 9H), 1.51-1.65 (m, 4H), 2.07-2.19 (m, 4H), 2.54 (s, 2H), 2.84-2.87 (m, 2H), 3.44-3.48 (m, 2H), 3.81 (s, 2H), 4.35 (s, 2H), 6.58 (s, 1H), 8.89 (s, 1H) |
| 1-4 | isobutyl | 35 | 0.50 (n-hexane:AcOEt = 1:1) | (CDCl$_3$): 1.02 (s, 9H), 1.37 (d, 6H), 1.47-1.50 (m, 2H), 2.04-2.20 (m, 4H), 2.51 (s, 2H), 2.84-2.87 (m, 2H), 3.82 (s, 2H), 4.35-4.37 (m, 3H), 6.61 (s, 1H), 8.89 (s, 1H) |
| 1-5 | morpholinopropyl | 42 | 0.20 (n-hexane:AcOEt = 1:1) | (CDCl$_3$): 1.01 (s, 9H), 1.51-1.54 (m, 2H), 2.07-2.17 (m, 4H), 2.40-2.50 (m, 4H), 2.52-2.55 (m, 4H), 2.83-2.86 (m, 2H), 3.57-3.61 (m, 6H), 3.81 (s, 2H), 4.35 (s, 2H), 6.58 (s, 1H), , 8.89 (s, 1H) |
| 1-6 | 4-fluorobenzyl | 50 | 0.40 (n-hexane:AcOEt = 1:1) | (CDCl3): 1.00 (s, 9H), 1.46-1.49 (m, 2H), 2.04-2.14 (m, 4H), 2.55 (s, 2H), 2.81-2.84 (m, 2H), 3.79 (s, 2H), 4.34 (s, 2H), 4.60 (s, 2H), 6.57 (s, 1H), 6.95-6.99 (m, 2H), 7.31-7.35 (m, 2H), 8.88 (s, 1H) |
| 1-7 | 2,4-difluorobenzyl | 26 | 0.250 (n-hexane:AcOEt = 1:1) | (CDCl3): 1.00 (s, 9H), 1.48-1.52 (m, 2H), 2.06-2.16 (m, 4H), 2.57 (s, 2H), 2.82-2.86 (m, 2H), 3.80 (s, 2H) 4.34 (s, 2H), 4.68 (s, 2H), 6.57 (s, 1H), 6.75-6.83 (m, 2H), 7.26-7.30 (m, 1H), 8.89 (s, 1H) |
| 1-8 | 2,4-dimethoxybenzyl | 19 | 0.40 (n-hexane:AcOEt = 1:1) | (CDCl3): 1.00 (s,9H), 1.47-1.51 (m, 2H) ,2.07-2.18 (m, 4H), 2.54 (s, 2H), 2.82-2.85 (m, 2H), 3.76 (s, 6H), 3.80 (s, 2H), 4.35 (s, 2H), 4.62 (s, 2H), 6.38-6.40 (m, 2H), 6.58 (s, 1H), 7.06 (d, 1H), 8.88 (s, 1H) |
| 1-9 | 3,4-dimethoxybenzyl | 23 | 0.40 (n-hexane:AcOEt = 1:1) | (CDCl3): 1.00 (s, 9H), 1.45-1.49 (m, 2H), 2.06-2.14 (m, 4H), 2.54 (s, 2H), 2.81-2.84 (m, 2H), 3.79 (s, 2H), 3.84 (s, 6H), 4.34 (s, 2H), 4.57 (s, 2H), 6.57 (s, 1H), 6.77 (d, 1H), 6.91-6.93 (m, 2H), 8.88 (s, 1H) |

Example 2

Example 2-0

Preparation 7-(2,2-Dimethyl-propyl)-6-(5methoxy-2-oxo-1,2-dihydro-1'H-spiro[indole-3,4'-piperidine]-1-ylmethyl)-7-pyrrole[2,3d]pyrimidine-2-carbonitrile

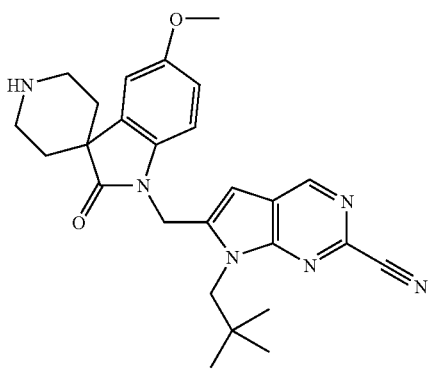

A. Preparation of 2-Fluoro-4-methoxy-1-nitro-benzene

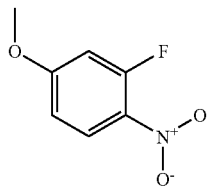

To a solution of 3-fluoro-4-nitro-phenol (25.3 g, 0.16 mol) in acetone (160 ml), potassium carbonate (41.7 g, 0.30 mol) and methyl iodide (20.0 ml, 0.32 mol) are added at ambient temperature. The reaction mixture is stirred at 40 C.° for 3 h. After cooling down to room temperature, dichloromethane is added to the reaction mixture, which is filtrated and evaporated. Dichloromethane is added to the residue and the organic phase is washed with H₂O and brine, dried over sodium sulfate and evaporated down to give 2-fluoro-4-methoxy-1-nitro-benzene in 98% yield.

Rf=0.5 (n-hexane:ethyl acetate=10:1).

$^1$H-NMR (400 MHz, CDCl$_3$) δ: 3.90 (s, 3H), 6.72-6.79 (m, 2H), 8.06-8.13 (m, 1H).

B. Preparation of 5-Methoxy-1,3-dihydro-indol-2-one

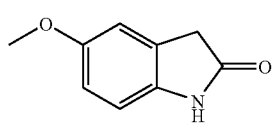

The title compound was prepared according to method reported in the patent (WO0206228).

To a solution of 2-fluoro-4-methoxy-1-nitro-benzene (84.1 g, 0.49 mol) and dimethyl malonate (129.9 g, 0.98 mol) in DMF (490 ml), potassium carbonate (135.9 g, 0.98 mol) is added at ambient temperature. The reaction mixture is stirred at 70 C.° for 12 h. The reaction mixture is added to toluene (393 ml) and 12 N HCl (123 ml) and extracted with ethyl acetate. The combined extracts are washed with H₂O and brine, dried over sodium sulfate and evaporated down to give 2-(5-methoxy-2-nitro-phenyl)-malonic acid dimethyl ester.

Rf=0.8 (n-hexane:AcOEt=1:1).

$^1$H-NMR (400 MHz, CDCl$_3$) δ: 3.80 (s, 6H), 3.89 (s, 3H), 5.45 (s, 1H), 6.94-6.96 (m, 2H), 8.15-8.20 (m, 1H).

To 2-(5-methoxy-2-nitro-phenyl)-malonic acid dimethyl ester and 5% Pd—C (7.0 g) in 1 l of flask, MeOH (490 ml) is added at ambient temperature. The reaction mixture is stirred under H₂ at room temperature for 15 h. The catalysts are removed by filtration and MeOH is evaporated down to give crude 5-methoxy-2-oxo-2,3-dihydro-1H-indole-3-carboxylic acid methyl ester.

Rf=0.10 (n-hexane:ethyl acetate=1:1).

To a solution of crude 5-methoxy-2-oxo-2,3-dihydro-1H-indole-3-carboxylic acid methyl ester in MeOH (320 ml), 6N HCl (255 ml, 1.92 mol) is added at ambient temperature. The reaction mixture is stirred at 70 C.° for 3 h. After cooling down to room temperature, 8 N KOH (269 ml, 1.82 mol) is added to reaction mixture. The reaction mixture is stirred at 40 C.° for 30 min. 12 N HCl (41 ml) is added to reaction mixture. MeOH is evaporated down and the white powder is filtrated.

Yield: 59% (three steps).

Rf=0.25 (n-hexane:AcOEt=1:1).

$^1$H-NMR (400 MHz, CDCl$_3$) δ: 3.51 (s, 2H), 3.78 (s, 3H), 6.72-6.85 (m, 3H), 7.60 (brs, 1H).

C. Preparation of 1'-Benzyl-5-methoxyspiro[indole-3,4'-piperidin]-2(1H)-one

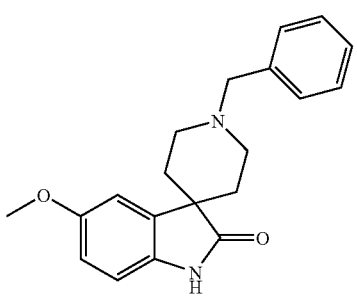

To a solution of NaHMDS (1 M THF solution) (800 ml, 0.8 mol), the solution of 5-methoxy-1,3-dihydro-indol-2-one (26.1 g, 0.16 mol) in THF (160 ml) and benzyl-bis-(2-chloroethyl)-amine (47.3 g, 0.18 mol) in THF (176 ml) are added at −78° C. The reaction mixture is stirred for 15 h at room temperature, quenched with saturated ammonium chloride and ice-water and extracted with ethyl acetate. The combined extracts are washed with brine, dried over sodium sulphate and evaporated down. Ethyl ether is added to the residue to give the powder, which is filtrated.

Yield: 39%

Rf=0.25 (n-hexane:AcOEt=1:1).

$^1$H-NMR (400 MHz, CDCl$_3$) δ: 1.81-1.99 (m, 2H), 2.00-2.04 (m, 2H), 2.66-2.72 (m, 2H), 2.90-2.96 (m, 2H), 3.67 (s, 2H), 3.77 (s, 3H), 6.71-6.81 (m, 2H), 7.00 (s, 1H), 7.25-7.40 (m, 5H), 8.32 (brs, 1H).

D. Preparation of tert-Butyl 5-methoxy-2-oxo-1,2-dihydro-1'H-spiro[indole-3,4'-piperidine]-1'-carboxylate

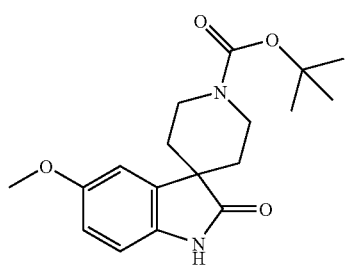

To 1'-benzyl-5-methoxyspiro[indole-3,4'-piperidin]-2(1H)-one (20.0 g, 62 mmol) and Pd/C (2.0 g) in 500 ml of flask, EtOH (120 ml) and acetic acid (5.5 ml) are added at ambient temperature. The reaction mixture is stirred under H$_2$ at room temperature for 15 h. The catalysts are removed by filtration and EtOH is evaporated down.

Rf=0.20 (n-hexane:AcOEt=1:1).

To a suspension of 5-methoxyspiro[indole-3,4'-piperidin]-2(1H)-one (9.9 g, 45.2 mmol) in dichloromethane (50 ml), 1N NaOH (45.2 ml, 45.2 mmol) and the solution of di-t-butyldicarbonate (9.3 g, 45.2 mmol) in dichloromethane (50 ml) are added at ambient temperature. The reaction mixture is stirred for 1 h. The reaction mixture is washed with brine, dried over magnesium sulfate and concentrated under vacuum. Chromatography on silica gel (eluent; n-hexane:ethyl acetate=2:1 and 1:1) gives 10.6 g of desired product.

Yield: 68% (two steps)

Rf=0.50 (n-hexane:AcOEt=1:1).

$^1$H-NMR (400 MHz, CDCl$_3$) δ: 1.51 (s, 9H), 1.76-1.89 (m, 4H), 3.70-3.90 (m, 7H), 6.74-6.76 (m, 1H), 6.83-6.88 (m, 2H), 8.83 (brs, 1H).

E. Preparation of 1-[2-Cyano-7-(2,2-dimethyl-propyl)-7H-pyrrolo[2,3-d]pyrimidin-6-ylmethyl]-5-methoxy-2-oxo-1,2-dihydro-1'H-spiro[indole-3,4'-piperidine]-1'carboxyric acid tert-butyl ester

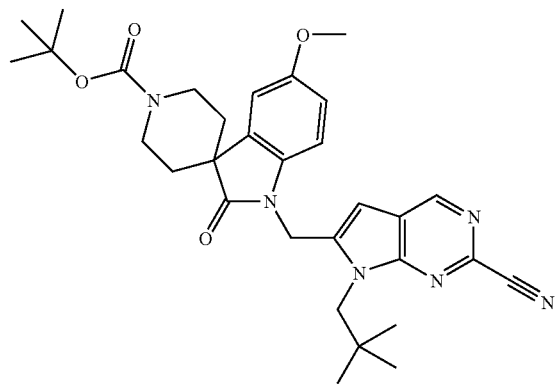

To a solution of tert-butyl 5-methoxy-2-oxo-1,2-dihydro-1'H-spiro[indole-3,4'-piperidine]-1'-carboxylate (10.6 g, 31.9 mmol) in DMF (70 ml), NaH (1.4 g, 35.1 mmol) are added at room temperature and the mixture is stirred at room temperature for 30 min. 6-Bromomethyl-7-(2,2-dimethyl-propyl)-7.H.-pyrrolo[2,3-.d.]pyrimidine-2-carbonitrile (9.5 g, 31.9 mmol) is added at 0° C. and the reaction mixture is stirred for 4 h at ambient temperature. The reaction mixture is quenched with ice-water and extracted with ethyl acetate. The combined extracts are washed with brine and dried over magnesium sulfate. Chromatography on silica gel (eluent; n-hexane:ethyl acetate=10:1 and 1:1) give 12.1 g of title product.

Yield: 68%

Rf=0.60 (n-hexane:ethyl acetate=1:1).

$^1$H-NMR (400 MHz, CDCl$_3$) δ: 1.09 (s, 9H), 1.50 (s, 9H), 1.83-1.86 (m, 4H), 3.78-3.84 (m, 7H), 4.22 (s, 2H), 5.13 (s, 2H), 6.37 (s, 1H), 6.62-6.65 (m, 1H), 6.72-6.75 (m, 1H), 7.26 (s, 1H), 8.84 (s, 1H).

F. Preparation of 7-(2,2-Dimethyl-propyl)-6-(5methoxy-2-oxo-1,2-dihydro-1'H-spiro[indole-3,4'-piperidine]-1-ylmethyl)-7-pyrrole[2,3d]pyrimidine-2-carbonitrile

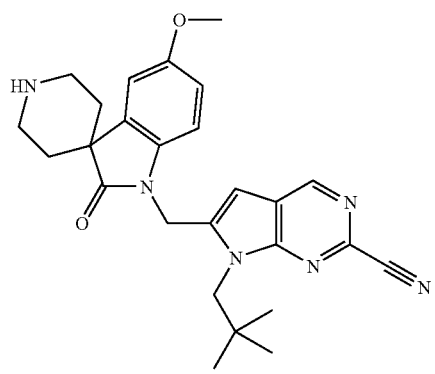

To a solution of 1-[2-cyano-7-(2,2-dimethyl-propyl)-7H-pyrrolo[2,3-d]pyrimidin-6-ylmethyl]-5-methoxy-2-oxo-1,2-dihydro-1'H-spiro[indole-3,4'-piperidine]-1'carboxyric acid tert-butyl ester (12.1 g, 21.6 mmol) in dichloromethane (100ml), TFA (5 ml) is added at 0° C. The reaction mixture is stirred at room temperature for 2 h. After removal of the solvent, saturated sodium bicarbonate is added to the residue and the mixture is extracted with ethyl acetate. The combined extracts are washed with brine, dried over magnesium sulfate and concentrated under vacuum. Ethyl ether is added to the residue, which is filtrated to give pale yellow product, 7-(2,2-Dimethyl-propyl)-6-(5methoxy-2-oxo-1,2-dihydro-1'H-spiro[indole-3,4'-piperidine]-1-ylmethyl)-7-pyrrole[2,3d]pyrimidine-2-carbonitrile.

Yield: 91%.

Rf=0.15 (CH$_2$Cl$_2$:MeOH=10:1).

$^1$H-NMR (400 MHz, CDCl$_3$) δ: 1.09 (s, 9H), 1.90-1.94 (m, 2H), 2.52-2.61 (m, 2H), 3.44-3.50 (m, 2H), 3.80 (s, 3H), 3.87-3.94 (m, 2H), 4.24 (s, 2H), 5.12 (s, 2H), 6.37 (s, 1H), 6.67 (d, 1H) 6.77-6.80 (m, 1H), 7.03 (s, 1H), 8.86 (s, 1H).

By repeating the procedures described above using appropriate starting materials and conditions the following compounds of formula I-(ii) are obtained as identified below in Table 2:

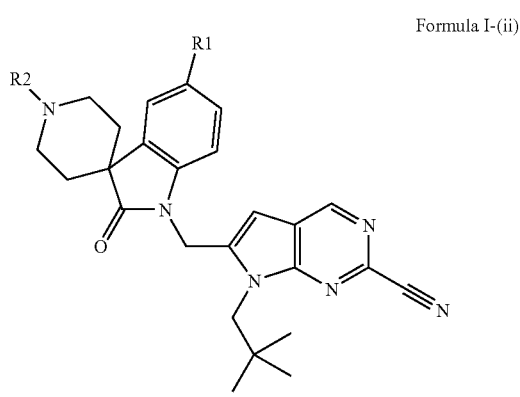

Formula I-(ii)

TABLE 2

| Example | R1 | R2 | Yield (%) | Rf(solvent) | $^1$H-NMR (400 MHz, δ) |
|---------|----|----|-----------|-------------|------------------------|
| 2-1 | H | H | 80 | 0.25 (MeOH:CH$_2$Cl$_2$ = 1:4) | (CDCl$_3$) : 1.10 (s, 9H), 1.84-1.89 (m, 4H), 3.07-3.13 (m, 2H), 3.38-3.44 (m, 2H), 4.24(s, 2H), 5.15 (s, 2H), 6.36 (s, 1H), 6.73 (d, 1H) 7.10 (t, 1H), 7.22 (t, 1H), 7.47 (d, 1H), 8.84 (s, 1H) |
| 2-2 | H | ╱ | 22 | 0.40 (MeOH:CH$_2$Cl$_2$ = 1:4) | (CDCl$_3$): 1.10 (s, 9H), 1.90-1.95 (m, 2H), 2.30-2.50 (m, 2H), 2.65 (brs, 3H), 2.95-3.35 (m, 4H), 4.24 (s, 2H), 5.14 (s, 2H), 6.36 (s, 1H), 6.74 (d, 1H), 7.13 (t, 1H), 7.22 (t, 1H), 7.43 (d, 1H), 8.84 (s, 1H) |
| 2-3 | H | ╱╲ | 14 | 0.40 (MeOH:CH$_2$Cl$_2$ = 1:4) | (CDCl$_3$):): 0.97 (t, 3H), 1.10 (s, 9H), 1.90-1.95 (m, 2H), 2.30-2.50 (m, 2H), 2.95-3.35 (m, 6H), 4.25 (s, 2H), 5.13 (s, 2H), 6.75 (d, 1H), 7.16 (t, 1H), 7.25 (t, 1H), 7.46 (d, 1H), 8.85 (s, 1H) |
| 2-4 | H | ⊥ | 27 | 0.45 (MeOH:CH$_2$Cl$_2$ = 1:4) | (CDCl$_3$): 1.10 (s, 9H), 1.24 (d, 6H), 1.92-2.00 (m, 2H), 2.15-2.30 (m, 2H), 2.90-3.13 (m, 3H), 3.15-3.25 (m, 2H), 4.24 (s, 2H), 5.14 (s, 2H), 6.35 (s, 1H), 6.72 7.20 (t, 1H), 7.46 (d, 1H), 8.83 (s, 1H) (s, 1H) |

TABLE 2-continued

| Example | R1 | R2 | Yield (%) | Rf(solvent) | $^1$H-NMR (400 MHz, δ) |
|---|---|---|---|---|---|
| 2-5 | H | n-propyl | 41 | 0.45 (MeOH:CH$_2$Cl$_2$ = 1:4) | (CDCl$_3$): 0.97 (t, 3H), 1.10 (s, 9H), 1.65-1.71 (m, 2H), 1.95-2.00 (m, 2H), 2.20-2.25 (m, 2H), 2.60-2.64 (m, 2H), 2.90-3.00 (m, 2H), 3.05-3.15 (m, 2H), 4.24 (s, 2H), 5.14 (s, 2H), 6.36 (s, 1H), 6.74 7.20 (t, 1H), 7.75 (d, 1H), 8.84 (s, 1H) |
| 2-6 | H | 3-morpholinopropyl | 33 | 0.15 (AcOEt only) | (CDCl$_3$): 1.11 (s, 9H), 1.90-3.10 (m, 16H), 3.70-3.80 (m, 4H), 4.25 (s, 2H), 5.16 (s, 2H), 6.37 (s, 1H), 6.74 (d, 1H), 7.31 (t, 1H), 7.24 (t, 1H), 7.45 (d, 1H), 8.85 (s, 1H) |
| 2-7 | H | 4-fluorobenzyl-CH$_2$ | 60 | 0.55 (MeOH:CH$_2$Cl$_2$ = 1:4) | (CDCl$_3$): 1.10 (s, 9H), 1.95-2.05 (m, 4H), 2.75-2.85 (m, 2H), 2.90-3.05 (m, 2H), 3.67 (brs, 2H), 4.23 (s, 2H) 5.14 (s, 2H), 6.35 (s, 1H), 6.72 (d, 1H), 7.02 (t, 1H), 7.09 (t, 1H), 7.21 (t, 1H), 7.35 (t, 2H) 7.43 (d, 1H), 8.83 (s, 1H) |
| 2-8 | H | acetonyl | 45 | 0.25 (AcOEt only) | (CDCl$_3$): 1.10 (s, 9H), 1.55-1.59 (m, 2H), 1.86-1.91 (m, 4H), 2.18 (s, 3H), 3.73-3.79 (m, 2H), 4.24 (s, 2H), 5.16 (s, 2H), 6.75 (d, 1H), 7.12 (t, 1H), 7.24 (t, 1H), 7.30 (d, 1H), 8.85 (s, 1H) |
| 2-9 | OMe | methyl | 16 | 0.40 (MeOH:CH$_2$Cl$_2$ = 1:4) | (CDCl$_3$): 1.09 (s, 9H), 1.93-2.10 (m, 4H), 2.50 (s, 3H), 2.75-2.85 (m, 2H), 2.90-3.10 (m, 2H), 3.77 (s, 3H), 4.22 (s, 2H), 5.12 (s, 2H), 6.36 (s, 1H), 6.62 (d, 1H), 6.73 (dd, 1H), 7.02 (d, 1H), 8.84 (s, 1H) |
| 2-10 | OMe | n-propyl | 37 | 0.23 (MeOH:CH$_2$Cl$_2$ = 1:4) | (DMSO): 1.04 (s, 9H), 1.07 (t, 3H), 1.82-1.90 (m, 4H), 2.44-2.53 (m, 2H), 2.6-2.69 (m, 2H), 2.78-2.87 (m, 2H), 3.72 (s, 3H), 4.27 (s, 2H), 5.23 (s, 2H), 6.43 (s, 1H), 6.79 (d, 1H), 6.83 (d, 1H), 7.15 (s, 1H), 9.02 (s, 1H), |
| 2-11 | F | H | 43 | 0.10 (n-hexane:AcOEt = 1:1) | (CDCl$_3$): 1.10 (s, 9H), 1.90-2.05 (m, 2H), 2.30-2.50 (m, 2H), 3.45-3.60 (m, 2H), 3.90-4.05 (m, 2H), 4.26 (s, 2H), 5.15 (s, 2H), 6.36 (s, 1H), 6.72 (dd, 1H), 6.99 (td, 1H), 7.12 (dd, 1H), 8.90 (s, 1H) |

TABLE 2-continued

| Example | R1 | R2 | Yield (%) | Rf(solvent) | $^1$H-NMR (400 MHz, δ) |
|---|---|---|---|---|---|
| 2-12 | ⟋F | ⟋ | 38 | 0.40 (MeOH:CH$_2$Cl$_2$ = 1:4) | (CDCl$_3$): 1.09 (s, 9H), 1.92-2.10 (m, 4H), 2.52 (s, 3H), 2.85-2.90 (m, 2H), 3.00-3.10 (m, 2H), 4.22 (s, 2H), 5.13 (s, 2H), 6.34 (s, 1H), 6.65 (dd, 1H), 6.92 (td, 1H), 7.16 (dd, 1H), 8.85 (s, 1H) |
| 2-13 | ⟋F | ⋀ | 27 | 0.38 (MeOH:CH$_2$Cl$_2$ = 1:5) | (DMSO): 1.04(s, 9H), 1.07(t, 3H), 1.82-1.95(m, 4H), 2.44-2.53(m, 2H), 2.6-2.7(m, 2H), 2.77-2.87(m, 2H), 4.27(s, 2H), 5.26(s, 2H), 6.44(s, 1H), 6.92-6.95 (m, 1H), 7.04-7.09 (m, 1H), 7.47-7.49 (m, 1H), 9.01 (s, 1H), |

Example 3

Example 3-0

Preparation of 7-(2,2-Dimethyl-propyl)-6-(1,3-dioxo-2,8-diaza-spiro[4.5]dec-2-ylmethyl)-7H-pyrrolo[2,3-d]pyrimidine-2-carbonitrile

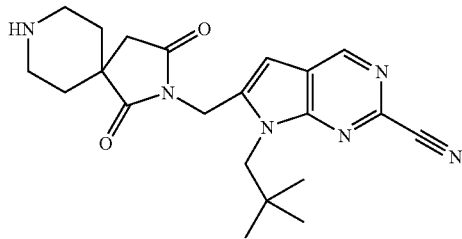

A. Preparation of 8-Benzyl-2,8-diaza-spiro[4.5]decane-1,3-dione

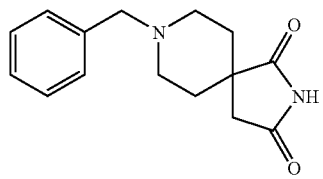

To a solution of 1-benzyl-piperidin-4-one (75.1 g, 0.40 mol) in toluene (400 ml), cyano-acetic acid ethyl ester (50.6 ml, 0.48 mol) and acetic acid (18.2 ml, 0.32 mol) are added at ambient temperature. The reaction mixture is refluxed for 4 h, quenched with ice-water and extracted with diethyl ether. The combined extracts are washed with H$_2$O, brine and dried over sodium sulphate to give (1-benzyl-piperidin-4-ylidene)-cyano-acetic acid ethyl ester in quantitative yield.

Rf=0.53 (n-hexane:AcOEt=1:1).
$^1$H-NMR (400 MHz, CDCl$_3$) δ: 1.30-1.37 (m, 3H), 2.58 (dd, 2H), 2.64 (dd, 2H), 2.79 (dd, 2H), 3.15 (dd, 2H), 3.55 (s, 2H), 4.23-4.32 (m, 2H), 7.21-7.36 (m, 5H).

To a solution of (1-benzyl-piperidin-4-ylidene)-cyanoacetic acid ethyl ester (112.9 g, 0.40 mol) in EtOH (500 ml) and H$_2$O (100 ml), potassium cyanide (64.6 g, 0.99 mol) is added at ambient temperature. The reaction mixture is stirred at 65 C.° for 24 h. After removal of EtOH, H$_2$O is added to the residue. The waster phase is extracted with diethyl ether. The combined extracts are washed with H$_2$O and brine, dried over sodium sulfate and evaporated down to give 77.7 g of 1-benzyl-4-cyanomethyl-piperidine-4-carbonitrile.

Rf=0.38 (n-hexane:AcOEt=1:1).
$^1$H-NMR (400 MHz, CDCl$_3$) δ: 1.76-1.81 (m, 2H), 2.10-2.05 (m, 2H), 2.23-2.39 (m, 2H), 2.69 (s, 2H), 2.90-2.94 (m, 2H), 3.56 (s, 2H), 7.21-7.38 (m, 5H).

Acetic acid (56.8 ml) and sulfuric acid (11.8 ml) are added to 1-benzyl-4-cyanomethyl-piperidine-4-carbonitrile (27.2 g, 0.114 mmol) at ambient temperature. The reaction mixture is stirred at 125 C.° for 1 h, cooled down to the room temperature and added to saturated NaOH aq. to adjust to pH 6.0. The mixture is extracted with dichloromethane. The combined extracts are washed with H$_2$O and brine, dried over sodium sulfate and evaporated down to give 8-benzyl-2,8-diaza-spiro[4.5]decane-1,3-dione (three steps yield: 81.8%).

Rf=0.40 (CH$_2$Cl$_2$:MeOH=10:1).
$^1$H-NMR (400 MHz, CDCl$_3$) δ: 1.52-1.57 (m, 2H), 2.02-2.17 (m, 4H), 2.59 (s, 2H), 2.86-2.90 (m, 2H), 3.52 (s, 2H), 7.21-7.28 (m, 2H), 7.30-7.37 (m, 3H), 7.92 (brs, 1H).

B. Preparation of 1,3-Dioxo-2,8-diaza-spiro[4.5]decane-8-carboxylic acid tert-butyl ester

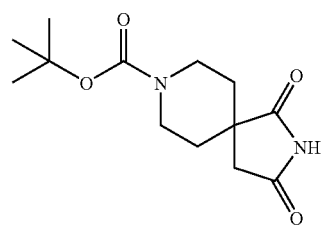

To 8-benzyl-2,8-diaza-spiro[4.5]decane-1,3-dione (28.3 g, 0.11 mol) and Pd(OH)$_2$ (8.5 g) in 2 l of flask, EtOH (438 ml) and acetic acid (5.5 ml) are added at ambient temperature. The reaction mixture is stirred under H$_2$ at room temperature for 15 h. The catalysts are removed by filtration and EtOH is evaporated down to give 2,8-diaza-spiro[4.5]decane-1,3-dione in quantitative yield. To a suspension of 2,8-diaza-spiro[4.5]decane-1,3-dione (4.2 g, 25.2 mmol) in dichloromethane (60 ml), 1N NaOH (26 ml, 26 mmol) and di-t-butyldicarbonate (6.1 g, 27.7 mmol) in dichloromethane (20 ml) are added at ambient temperature. The reaction mixture is stirred for 15 h. 10% Citric acid is added to the reaction mixture and the pH of the mixture is adjusted to 5. The combined extracts are washed with brine, dried over magnesium sulfate and concentrated under vacuum to give solid product, which filtrated with diethyl ether.

Yield: 51%

Rf=0.25 (n-hexane:ethyl acetate=1:1).

$^1$H-NMR (400 MHz, CDCl$_3$) δ: 1.47 (s, 9H), 1.55-1.70 (m, 2H), 1.95-2.05 (m, 2H), 2.62 (s, 2H), 2.96-3.02 (m, 2H), 4.02-4.04 (m, 2H), 8.14 (brs, 1H).

C. Preparation of 2-[2-Cyano-7-(2,2-dimethyl-propyl)-7H-pyrrolo[2,3-d]pyrimidin-6-ylmethyl]-1,3-dioxo-2,8-diaza-spiro[4.5]decane-8-carboxylic acid tert-butyl ester

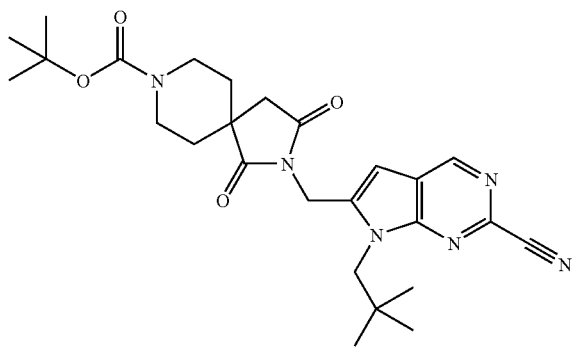

6-Bromomethyl-7-(2,2-dimethyl-propyl)-7H-pyrrolo[2,3-d]pyrimidine-2-carbonitrile (1.0 g, 3.25 mmol) and 1,3-dioxo-2,8-diaza-spiro[4.5]decane-8-carboxylic acid tert-butyl ester (0.82 g, 3.42 mmol) are dissolved in DMF (15 ml) and potassium carbonate (0.58 g, 4.23 mmol) is added to the solution. The reaction mixture is stirred at room temperature for 15 h and quenched with saturated ammonium chloride and extracted with ethyl acetate. The combined extracts are washed with H$_2$O, brine and dried over magnesium sulfate. Chromatography on silica gel (eluent; n-hexane:ethyl acetate=2:1) gives 1.56 g of desired 2-[2-cyano-7-(2,2-dimethyl-propyl)-7H-pyrrolo[2,3-d]pyrimidin-6-ylmethyl]-1,3-dioxo-2,8-diaza-spiro[4.5]decane-8-carboxylic acid tert-butyl ester in 97% yield.

Rf=0.30 (n-hexane:ethyl acetate=1:1).

$^1$H-NMR (400 MHz, CDCl$_3$) δ: 0.99 (s, 9H), 1.40 (s, 9H), 1.66-1.68 (m, 4H), 2.89-2.93 (m, 2H), 3.85-3.88 (m, 2H), 4.25 (s, 2H), 4.90 (s, 2H), 6.62 (s, 1H), 9.06 (s, 1H).

D. Preparation of 7-(2,2-Dimethyl-propyl)-6-(1,3-dioxo-2,8-diaza-spiro[4.5]dec-2-ylmethyl)-7H-pyrrolo[2,3-d]pyrimidine-2-carbonitrile

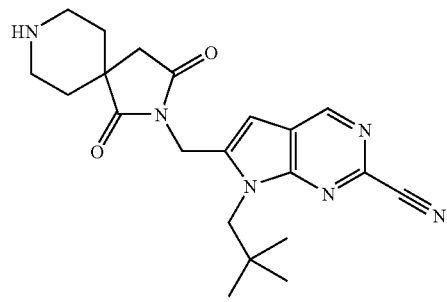

To a solution of 2-[2-cyano-7-(2,2-dimethyl-propyl)-7H-pyrrolo[2,3-d]pyrimidin-6-ylmethyl]-1,3-dioxo-2,8-diaza-spiro[4.5]decane-8-carboxylic acid tert-butyl ester (1.5 g, 3.1 mmol) in dichloromethane (20 ml), TFA (5 ml) is added at 0° C. The reaction mixture is stirred at room temperature for 2 h. After removal of the solvent, saturated sodium bicarbonate is added to the residue and the mixture is extracted with dichloromethane. The combined extracts are washed with H$_2$O, brine, dried over magnesium sulfate and concentrated under vacuum to give desired product, 7-(2,2-dimethyl-propyl)-6-(1,3-dioxo-2,8-diaza-spiro[4.5]dec-2-ylmethyl)-7H-pyrrolo[2,3-d]pyrimidine-2-carbonitrile.

Yield: 91%.

Rf=0.15 (CH$_2$Cl$_2$:MeOH=10:1).

$^1$H-NMR (400 MHz, CDCl$_3$) δ: 1.03 (s, 9H), 1.44-1.51 (m, 2H), 1.69 (brs, 1H), 1.95-2.02 (m, 2H), 2.66 (s, 2H), 2.69-2.72 (m, 2H), 3.11-3.17 (m, 2H), 4.34 (s, 2H), 4.91 (s, 2H), 6.59 (s, 1H), 8.90 (s, 1H).

By repeating the procedures described above using appropriate starting materials and conditions the following compounds of formula I-(iii) are obtained as identified below in Table 3.

Formula I-(iii)

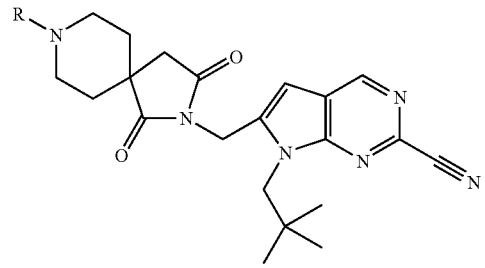

TABLE 3

| Example | Rx | Yield (%) | Rf(Solvent) | NMR(400 MHz, δ) |
|---|---|---|---|---|
| 3-1 | cyclohexyl-NH-C(=O)-CH3 | 41 | 0.55 (MeOH:CH$_2$Cl$_2$ = 1:10) | (CDCl$_3$): 1.02 (s, 9H), 1.06-1.16 (m, 3H), 1.31-1.42 (m, 2H), 1.52-1.72 (m, 6H), 1.92-2.02 (m, 3H), 2.64 (s, 2H), 2.98-3.05 (m, 2H), 3.61-3.65 (m, 1H), 3.84-3.90 (m, 2H), 4.28-4.30 (m, 1H), 4.33 (s, 2H), 4.92 (s, 2H), 6.60 (s, 1H), 8.90 (s, 1H) |
| 3-2 | CH3-NH-C(=O)-CH3 | 46 | 0.50 (MeOH:CH$_2$Cl$_2$ = 1:10) | (CDCl$_3$): 1.02 (s, 9H), 1.53-1.56 (m, 2H), 1.97-2.03 (m, 2H), 2.65 (s, 2H), 2.81 (d, 3H, ), 3.01-3.08 (m, 2H), 3.86-3.91 (m, 2H), 4.33 (s, 2H), 4.52-4.52 (m, 1H), 4.92 (s, 2H), 6.60 (s, 1H), 8.90 (s, 1H) |
| 3-3 | 2,4-dimethoxy-methylbenzene | 28 | 0.30 (n-hexane:AcOEt = 1:1) | (CDCl$_3$):): 1.03 (s, 9H), 1.55-1.68 (m, 3H), 2.29-2.36 (m, 2H), 2.60-2.68 (m, 3H), 3.36-3.40 (m, 2H), 3.77 (s, 3H), 3.84 (s, 3H), 4.34 (s, 2H), 4.93 (s, 2H), 6.41 (d, 1H), 6.45 (s, 1H), 6.49 (s, 1H), 6.85 (d, 1H), 8.90 (s, 1H) |
| 3-4 | acetone | 54 | 0.45 (MeOH:CH$_2$Cl$_2$ = 1:10) | (CDCl$_3$): 1.02 (s, 9H), 1.52-1.68 (m, 2H), 1.94-2.06 (m, 3H), 2.11 (s, 3H), 2.68 (d, 2H), 3.05-3.15 (m, 1H), 3.25-3.35 (m, 1H), 3.83-3.95 (m, 1H), 4.28-4.36 (m, 3H), 4.93 (s, 2H), 6.61 (s, 1H), 8.90 (s, 1H) |
| 3-5 | ethylbenzene | 62 | 0.35 (n-hexane:AcOEt = 1:1) | (CDCl$_3$): 1.02 (s, 9H), 1.45-1.50 (m, 2H), 2.00-2.14 (m, 4H), 2.60 (s, 2H), 2.86-2.90 (m, 2H), 3.52 (s, 2H), 4.32 (s, 2H), 4.90 (s, 2H), 6.58 (s, 1H), 7.25-7.32 (m, 5H), 8.89 (s, 1H) |
| 3-6 | morpholinyl-CH2-C(=O)-CH3 | 30 | 0.20 (n-hexane:AcOEt = 1:1) | (CDCl3): 1.03 (s, 9H), 1.55-1.60 (m, 2H), 1.90-2.10 (m, 2H), 2.45-2.55 (m, 4H), 2.68 (brs, 2H), 3.09-3.31 (m, 4H), 3.70-3.72 (m, 4H), 4.09-4.14 (m, 2 H), 4.34 (s, 2H), 4.93 (s, 2H), 6.61 (s, 1H), 8.90 (s, 1H) |

Example 4

Example 4-0

Preparation of 6-(8-Acetyl-2,8-diaza-spiro[4.5]dec-2-ylmethyl)-7-(3,3-dimethyl-butyl)-7H-pyrrolo[2,3-d]pyrimidine-2-carbonitrile

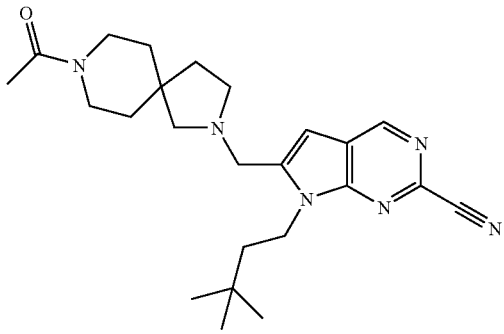

8-Methanesulfonyl-2,8-diaza-spiro[4.5]decane hydrochloride

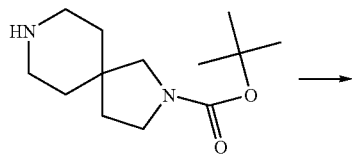

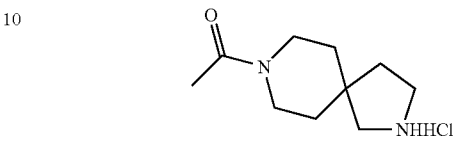

To a solution of 2,8-diaza-spiro[4.5]decane-2-carboxylic acid tert-butyl ester (1.12 g, 4.66 mol) in CH$_2$Cl$_2$ (10 ml), triethylamine (3.88 ml) and methanesulfonyl chloride (1.08 ml, 14 mmol) are added at 0° C. The reaction mixture is stirred for overnight, quenched with ice-water and extracted with dichloromethane. The combined extracts are washed with H$_2$O, brine and dried over sodium sulphate to give crude 8-methane sulfonyl-2,8-diaza-spiro[4.5]decane-2-carboxylic acid tert-butyl ester (1.32 g).

Rf=0.7 (CH$_2$Cl$_2$:MeOH=10:1). $^1$H-NMR (400 MHz, CDCl$_3$) δ: 1.46(s, 9H), 1.66-1.76(m, 6H), 2.76-2.80(m, 2H), 3.00(s, 3H), 3.15-3.25(m, 2H), 3.36-3.45(m, 4H).

To a solution of 8-methanesulfonyl-2,8-diaza-spiro[4.5]decane-2-carboxylic acid tert-butyl ester (1.32 g) in ethyl acetate (10 ml), a 1 M ethyl acetate solution of HCl (20 ml). After stirring for 2 h at room temperature, solvent is evaporated down to give 8-methanesulfonyl-2,8-diaza-spiro[4.5]decane hydrochloride as a solid.

Rf=0.05 (ethyl acetate only). $^1$H-NMR (400 MHz, DMSO-d$_6$) δ: 1.62-1.68(m, 4H), 1.78-1.82(m, 2H), 2.87(s, 3H), 2.98-3.12(m, 6H), 3.20-3.23(m, 2H), 9.49(brs, 1H), 9.59(brs, 1H).

1-(2,8-Diaza-spiro[4.5]dec-8-yl)-ethanone hydrochloride

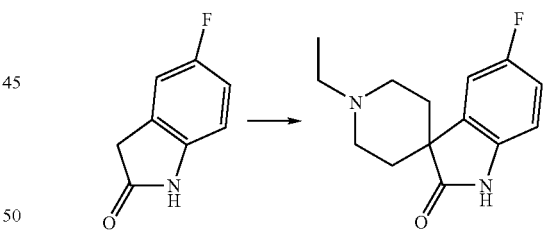

To a solution of 2,8-diaza-spiro[4.5]decane-2-carboxylic acid tert-butyl ester (1.12 g, 4.66 mol) in dichloromethane (10 ml), triethylamine (3.88 ml) and acetic anhydride (1.32 ml, 14 mmol) are added at 0° C. The reaction mixture is stirred for overnight, quenched with ice-water and extracted with dichloromethane. The combined extracts are washed with H$_2$O, brine and dried over sodium sulphate to give crude 8-acetyl-2,8-diaza-spiro[4.5]decane-2-carboxylic acid tert-butyl ester (1.34 g).

Rf=0.6 (CH$_2$Cl$_2$:MeOH=10:1) $^1$H-NMR (400 MHz, CDCl$_3$) δ: 1.46(s, 9H), 1.50-1.56(m, 4H), 1.72-1.76(m, 2H), 2.03(s, 2H), 2.22(s, 3H), 3.16-3.49(m, 6H).

To a solution of 8-acetyl-2,8-diaza-spiro[4.5]decane-2-carboxylic acid tert-butyl ester (1.34 g) in ethyl acetate (10 ml), a 1 M ethyl acetate solution of HCl (20 ml). After stirring for 2 h at room temperature, the reaction mixture is evaporated down to give 1-(2,8-diaza-spiro[4.5]dec-8-yl)-ethanone hydrochloride as a solid.

Rf=0.05 (ethyl acetate only). $^1$H-NMR (400 MHz, DMSO-d$_6$) δ: 1.44-1.59(m, 4H), 1.76-1.83(m, 2H), 2.07(s, 3H), 2.96-3.06(m, 2H), 3.16-3.24(m, 4H), 3.38-3.56(m, 2H), 9.55(brs, 1H), 9.67(brs, 1H).

Intermediate I

To a solution of 5-methoxy-1,3-dihydro-indol-2-one (1.5 g, 10 mmol) in THF (160 ml), a solution of NaHMDS (1 M THF solution) (50 ml, 50 mmol) is added at −78° C. After stirring for 30 min at −78° C., ethyl-bis-(2-chloro-ethyl)-amine (47.3 g, 0.18 mol) in THF (176 ml) is added and the reaction mixture is stirred for 15 h at room temperature, quenched with sat.NH$_4$Claq. and ice-water and extracted with ethyl acetate. The combined extracts are washed with brine, dried over sodium sulphate and evaporated down. Ethyl ether is added to the residue to give the powder, which is filtrated.

Rf=0.10 (CH$_2$Cl$_2$:MeOH=30:1) $^1$H-NMR 400 MHz, CDCl$_3$) δ: 1.17(t, 3H), 1.87-2.02(m, 4H), 2.60(q, 2H), 2.69-2.74(m, 2H), 2.90-2.96(m, 2H), 6.78-6.82(m, 1H), 6.88-6.93 (m, 1H), 7.08-7.11 (m, 1H), 8.04(brs, 1H).

Intermediate L

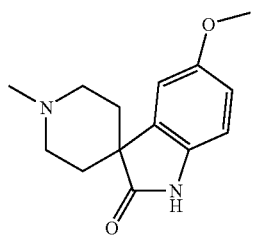

To a solution of 5-Methoxy-1,3-dihydro-indol-2-one (1.06 g, 6.49 mmol) in THF (13 ml), a solution of NaHMDS (1 M THF solution) (32.5 ml, 32.5 mmol) is added at −78° C. After stirring for 30 min at −78° C., methyl-bis-(2-chloro-ethyl)-amine hydrochloride (1.37 g, 7.14 mol) is added and the reaction mixture is stirred for 13.5 h at room temperature, quenched with sat.NH₄Claq. and ice-water and extracted with ethyl acetate. The organic extracts are washed with brine, dried over sodium sulphate and evaporated down. Ethyl ether is added to the residue to give the powder, which is filtrated.

Rf=0.10 (CH$_2$Cl$_2$:MeOH=30:1) $^1$H-NMR (400 MHz, DMSO-d$_6$) δ: 1.66-1.78(m, 4H), 2.28(s, 3H), 2.44-2.47(m, 2H), 2.71-2.77(m, 2H), 3.70(s, 3H), 6.74(s, 2H), 7.01(s, 1H), 10.15(brs, 1H).

Intermediate

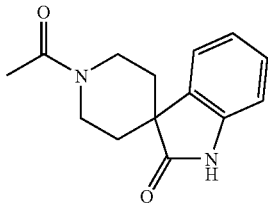

To a solution of intermediate (422 mg, 1.76 mol) in dichloromethane (5 ml), triethylamine (1.2 ml) and acetic anhydride (0.33 ml, 3.53 mmol) are added at 0° C. The reaction mixture is stirred for 2 h, and is quenched with ice-water and extracted with dichloromethane. The combined organic layer is washed with water and brine, dried over MgSO$_4$, and concentrated in vacuo. The residue is purified by silica gel column chromatography (n-hexane:AcOEt=5:1) to give the product.

Rf=0.6 (CH$_2$Cl$_2$:MeOH=10:1) $^1$H-NMR (400 MHz, CDCl$_3$) δ: 1.79-1.95(m, 4H), 2.20(s, 3H), 3.68-3.74(m, 1H), 3.80-3.87(m, 1H), 3.98-4.22(m, 2H), 6.90-6.92(m, 1H), 7.03-7.07(m, 1H), 7.22-7.26(m, 2H), 8.06(brs, 1H).

6-(8-Acetyl-2,8-diaza-spiro[4.5]dec-2-ylmethyl)-7-(3,3-dimethyl-butyl)-7H-pyrrolo[2,3-d]pyrimidine-2-carbonitrile

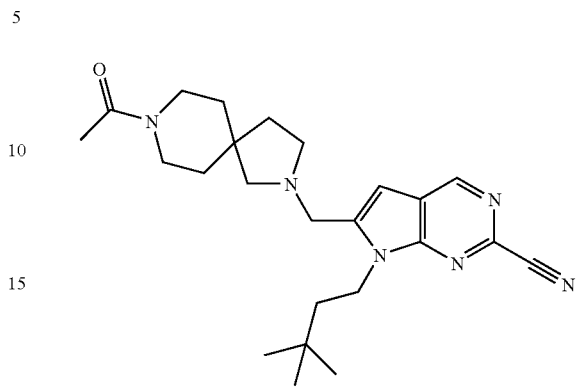

To a solution of 6-bromomethyl-7-(3,3-dimethyl-butyl)-7H-pyrrolo[2,3-d]pyrimidine-2-carbonitrile (440 mg, 1.37 mmol) in DMF (5 ml), 1-(2,8-diaza-spiro[4.5]dec-8-yl)-ethanone hydrochloride (300 mg, 1.37 mmol) and K$_2$CO$_3$ (568 mg, 4.11 mmol) and triethylamine (5 ml) are added. The mixture is stirred at room temperature under nitrogen atomosphere for 11 h. The reaction mixture is diluted with water and extracted with AcOEt (twice). The combined organic layers are washed with water and brine, dried over MgSO$_4$, and concentrated in vacuo. The residue is purified by silica gel column chromatography (n-hexane:AcOEt=1:1) to give the product.

Rf=0.30 (n-hexane:AcOEt=1:1). $^1$H-NMR (400 MHz, CDCl$_3$) δ: 1.05(s, 9H), 1.53-1.72(m, 8H), 2.07(s, 3H), 2.40-2.48(m, 2H), 2.60-2.69(m, 2H), 3.35-3.45(m, 2H), 3.60-3.67(m, 1H), 3.74-3.82(m, 2H), 4.40-4.44(m, 2H), 6.49(s, 1H), 8.87(s, 1H).

By repeating the procedures described above using appropriate starting materials and conditions the following compounds of formula I-iv are obtained as identified below in Table 4.

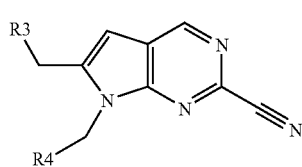

Formula 1-iv

TABLE 4

| Example | R3 | R4 | Rf(solvent) | NMR(400 MHz, CDCl3, □) |
|---|---|---|---|---|
| 4-1 | ![R3 structure: acetyl-diazaspiro] | ![R4 structure: 4-chlorobenzyl] | 0.80 (n-hexane: AcOEt = 1:1) | 1.50-1.71(m, 6H), 2.06(s, 3H), 2.32-2.41(m, 2H), 2.48-2.65 (m, 2H), 3.10-3.14(m, 2H), 3.29-3.52(m, 5H), 3.62-3.69 (m, 1H), 4.58-4.61(m, 2H), 6.46(s, 1H), 6.99-7.01(m, 2H), 7.23-7.26 (m, 2H), 8.89 (s, 1H). |

TABLE 4-continued

| Example | R3 | R4 | Rf(solvent) | NMR(400 MHz, CDCl3, ☐) |
|---|---|---|---|---|
| 4-2 | (methylsulfonyl-substituted diazaspiro structure with N-methyl) | 4-chlorobenzyl | 0.70 (n-hexane: AcOEt = 1:1) | 1.53-1.55(m, 2H), 1.63-1.70(m, 6H), 2.35(s, 2H), 2.56-2.60(m, 2H), 2.75(s, 3H), 3.05-3.13(m, 2H), 3.20-3.26(m, 2H), 3.46(s, 2H), 4.57-4.61(m, 2H), 6.45(s, 1H), 6.97-6.99(m, 2H), 7.22-7.25(m, 2H), 8.90(s, 1H). |
| 4-3 | (methylsulfonyl-substituted diazaspiro structure with N-methyl) | neopentyl | 0.80 (n-hexane: AcOEt = 1:1) | 1.04(s, 9H), 1.66-1.70(m, 8H), 2.43(brs, 2H), 2.62-2.65(m, 2H), 2.75(s, 3H), 3.09-3.15(m, 2H), 3.20-3.25(m, 2H), 3.78(s, 2H), 4.39-4.43(m, 2H), 6.49(s, 1H), 8.88(s, 1H). |
| 4-4 | (N-benzyl diazaspiro structure with N-methyl) | cyclohexylmethyl | 0.30 (n-hexane: AcOEt = 1:1) | 0.97-1.03(m, 2H), 1.15-1.34(m, 5H), 1.56-1.80(m, 12H), 2.35-2.40(m, 6H), 2.55-2.58(m, 2H), 3.45(s, 2H), 3.75(s, 2H), 4.38-4.41(m, 2H), 6.47(s, 1H), 7.29-7.30(m, 5H), 8.86(s, 1H). |
| 4-5 | (2,4-dioxo spiropiperidine with N-methyl) | 4-chlorobenzyl | 0.13 (n-hexane: AcOEt = 1:1) | 1.53-1.60(m, 4H), 2.09-2.16(m, 4H), 2.59(s, 2H), 2.80-2.83(m, 2H), 3.12-3.14(m, 2H), 3.37(s, 2H), 4.55-4.64(m, 2H), 6.47(s, 1H), 6.99-7.03(m, 2H), 7.23-7.26(m, 2H), 7.75(brs, 1H), 8.90(s, 1H). |
| 4-6 | (5-fluoro spiroindolin-2-one with N-ethyl piperidine) | cyclohexylmethyl | 0.10 (n-hexane: AcOEt = 1:1) | 0.98-1.39(m, 9H), 1.65-1.82(m, 7H), 1.99-2.03(m, 4H), 2.59-2.64(m, 2H), 2.98(m, 2H), 4.36-4.39(m, 2H), 5.10(s, 2H), 6.40(s, 1H), 6.69-6.72(m, 1H), 6.88-6.93(m, 1H), 7.16-7.18(m, 1H), 8.86(s, 1H). |
| 4-7 | (5-methoxy spiroindolin-2-one with N-methyl piperidine) | cyclohexylmethyl | 0.10 (n-hexane: AcOEt = 1:1) | 0.97-1.39(m, 6H), 1.60-1.82(m, 8H), 1.98-2.00(m, 3H), 2.46(s, 3H), 2.71-2.74(m, 2H), 2.92-2.94(m, 2H), 3.77(s, 3H), 4.36-4.40(m, 2H), 5.09(s, 2H), 6.40(s, 1H), 6.66-6.73(m, 2H), 7.02(d, 1H), 8.85(s, 1H). |
| 4-8 | (N-acetyl spiroindolin-2-one piperidine) | cyclohexylmethyl | 0.30 (n-hexane: AcOEt = 1:1) | 1.02-1.42(m, 6H), 1.68-1.95(m, 11H), 2.12(s, 3H), 3.75-3.85(m, 2H), 4.01-4.07(m, 1H), 4.24-4.29(m, 1H), 4.40-4.44(m, 2H), 5.16(s, 2H), 6.44(s, 1H), 6.84-6.86(m, 1H), 7.11-7.15(m, 1H), 7.24-7.33(m, 2H), 8.85(s, 1H). |

TABLE 4-continued

| Example | R3 | R4 | Rf(solvent) | NMR(400 MHz, CDCl3, δ) |
|---|---|---|---|---|
| 4-9 | (1-acetylpiperidine spiro 1-methylindolin-2-one) | neopentyl | 0.35 (n-hexane: AcOEt = 1:1) | 1.09(s, 9H), 1.70-1.74(m, 2H), 1.88-1.94(m, 4H), 2.19(s, 3H), 3.74-3.81(m, 2H), 4.04-4.14(m, 1H), 4.26-4.29(m, 1H), 4.38-4.42(m, 2H), 5.13(s, 2H), 6.38 (s, 1H), 6.80(d, 1H), 7.11-7.15 (m, 1H), 7.23-7.32(m, 2H), 8.85 (s, 1H). |
| 4-10 | (1-acetylpiperidine spiro 1-methylindolin-2-one) | (4,4-difluorocyclohexyl)ethyl | 0.30 (n-hexane: AcOEt = 1:1) | 1.38-1.93(m, 13H), 2.08-2.17 (m, 2H), 2.19(s, 3H), 3.72-3.84 (m, 2H), 3.99-4.06(m, 1H), 4.23-4.29(m, 1H), 4.41-4.45(m, 2H), 5.12(s, 2H), 6.48(s, 1H), 6.84-6.86(m, 1H), 7.11-7.15 (m, 1H), 7.24-7.32(m, 2H), 8.89(s, 1H) |
| 4-11 | (1-ethylpiperidine spiro 1-methylindolin-2-one) | (4,4-difluorocyclohexyl)ethyl | 0.20 (n-hexane: AcOEt = 1:1) | (DMSO-d$_6$) 1.07(t, 3H), 1.24-1.46(m, 3H), 1.69-2.02(m, 12H), 2.60-2.75 (m, 2H), 2.80-2.90(m, 2H), 3.25-3.36(m, 2H), 4.40-4.44(m, 2H), 5.26(s, 2H), 6.54(s, 1H), 7.04-7.09(m, 2H), 7.22-7.25(m, 1H), 7.55-7.57(m, 1H), 9.02(s, 1H). |
| 4-12 | (3-methyl-8-methyl-1,3,8-triazaspiro[4.5]decane-2,4-dione) | cyclohexylethyl | 0.09 (n-hexane: AcOEt = 1:1) | CDCl3 0.98-1.07(m, 2H), 1.18-1.41(m, 4H), 1.68-1.84(m, 9H), 2.11-2.16(m, 2H), 2.27-2.32(m, 2H), 2.92-2.99(m, 2H), 3.03(s, 3H), 3.73-3.78(m, 2H), 4.40-4.44(m, 2H), 5.84(brs, 1H), 6.53(s, 1H), 8.89(s, 1H) |

Example 4-13

Preparation of 3-[2-Cyano-7-(2-cyclohexyl-ethyl)-7H-pyrrolo[2,3-d]pyrimidin-6-ylmethyl]-4-oxo-1-phenyl-1,3,8-triaza-spiro[4.5]decane-8-carboxylic acid tert-butyl ester

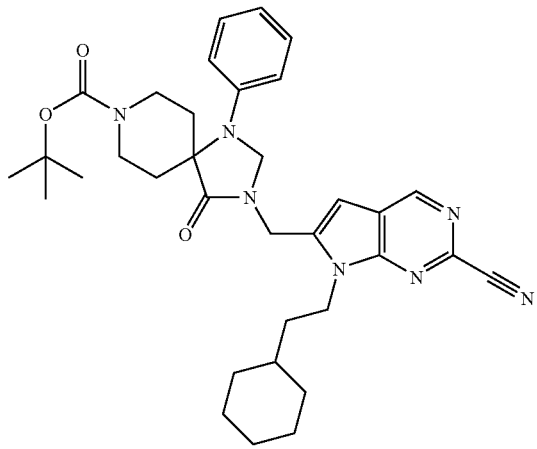

4-Oxo-1-phenyl-1,3,8-triaza-spiro[4.5]decane-8-carboxylic acid tert-butyl ester

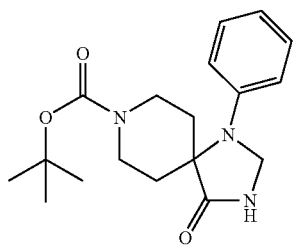

To a suspension of 1-phenyl-1,3,8-triaza-spiro[4.5]decan-4-one (1.0 g, 4.32 mmol) in dichloromethane (10 ml), saturated sodium bicarbonate solution (10 ml) and di-t-butyldicarbonate (1.04 g, 4.76 mmol) in dichloromethane (5 ml) are added at ambient temperature. The reaction mixture is stirred for 1 h and quenched with H$_2$O and extracted with ethyl acetate. The combined extracts are washed with H$_2$O and brine, dried over sodium sulfate and evaporated down to give 4-oxo-1-phenyl-1,3,8-triaza-spiro[4.5]decane-8-carboxylic acid tert-butyl ester. Yield: 100%

Rf=0.90(CH$_2$Cl$_2$:MeOH=20:1) $^1$H-NMR(400 MHz, CDCl$_3$) δ: 1.51(s, 9H), 1.63-1.71(m, 2H), 2.50-2.65(m, 2H), 3.50-3.65(m, 2H), 3.97-4.10(m, 2H), 4.75(s, 2H), 6.74-6.76(m, 2H), 6.84-6.88(m, 1H), 7.01(brs, 1H), 7.23-7.27(m, 2H).

3-[2-Cyano-7-(2-cyclohexyl-ethyl)-7H-pyrrolo[2,3-d]pyrimidin-6-ylmethyl]4-oxo-1-phenyl-1,3,8-triaza-spiro[4.5]decane-8-carboxylic acid tert-butyl ester

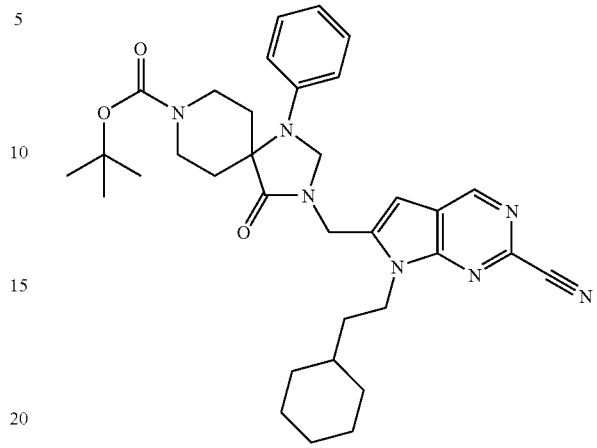

To a solution of 6-chloromethyl-7-(2-cyclohexyl-ethyl)-7H-pyrrolo[2,3-d]pyrimidine-2-carbonitrile (600 mg, 1.98 mmol) in DMF (7 ml), 4-oxo-1-phenyl-1,3,8-triaza-spiro[4.5]decane-8-carboxylic acid tert-butyl ester (657 mg, 1.98 mmol) and sodium hydride (101 mg, 2.53 mmol) are added. The mixture is stirred at room temperature under nitrogen atomosphere for 14 h. The reaction mixture is diluted with water and extracted with AcOEt (twice). The combined organic layers are washed with water and brine, dried over MgSO$_4$, and concentrated in vacuo. The residue is purified by silica gel column chromatography (n-hexane:AcOEt=1:1) to give the product in 29% yield.

Rf=0.25(n-hexane:AcOEt=1:1). $^1$H-NMR(400 MHz, CDCl$_3$) δ: 0.97-1.49(m, 7H), 1.50(s, 9H), 1.56-1.82(m, 8H), 2.45-2.60(m, 2H), 3.50-3.65(m, 2H), 4.09-4.14(m, 2H), 4.33-4.36(m, 2H), 4.64(s, 2H), 4.87(s, 2H), 6.72-6.74(m, 2H), 6.86-6.90(m, 1H), 7.20-7.24(m, 2H), 8.94(s, 1H).

Example 4-14

7-(2-Cyclohexyl-ethyl)-6-(4-oxo-1-phenyl-1,3,8-triaza-spiro[4.5]dec-3-ylmethyl)-7H-pyrrolo[2,3-d]pyrimidine-2-carbonitrile trifluoroacetic acid salt

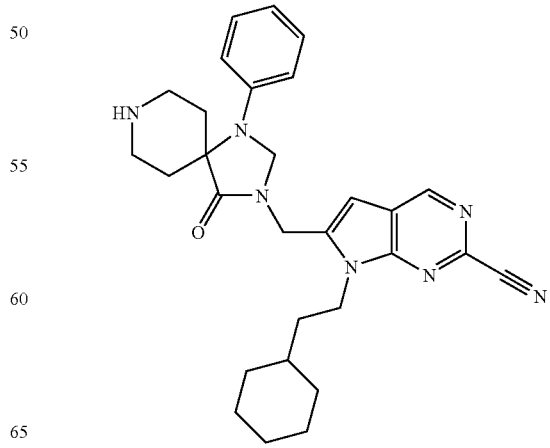

To a solution of 3-[2-cyano-7-(2-cyclohexyl-ethyl)-7H-pyrrolo[2,3-d]pyrimidin-6-ylmethyl]4-oxo-1-phenyl-1,3,8-triaza-spiro[4.5]decane-8-carboxylic acid tert-butyl ester (340 mg, 0.56 mmol) in dichloromethane (5 ml), trifluoroacetic acid (5 ml) is added. After stirring for 1 h at room temperature, solvent is evaporated down to give 7-(2-cyclohexyl-ethyl)-6-(4-oxo-1-phenyl-1,3,8-triaza-spiro[4.5]dec-3-ylmethyl)-7H-pyrrolo[2,3-d]pyrimidine-2-carbonitrile trifluoroacetic acid salt in quant yield.

Rf=0.10 (CH$_2$Cl$_2$:MeOH=20:1) $^1$H-NMR (400 MHz, CDCl$_3$) δ: 0.98-1.38(m, 5H), 1.65-1.83(m, 8H), 1.98-2.09(m, 2H), 2.71-2.80(m, 2H), 3.53-3.56(m, 2H), 3.94-4.02(m, 2H), 4.38-4.42(m, 2H), 4.73(s, 2H), 4.91(s, 2H), 6.71(s, 1H), 6.88-6.90(m, 2H), 7.01-7.04(m, 1H), 7.28-7.32(m, 2H), 7.85(brs, 1H), 8.25(brs, 1H), 9.08(s, 1H).

Example 4-15

6-(8-Acetyl-4-oxo-1-phenyl-1,3,8-triaza-spiro[4.5]dec-3-ylmethyl)-7-(2-cyclohexyl-ethyl)-7H-pyrrolo[2,3-d]pyrimidine-2-carbonitrile

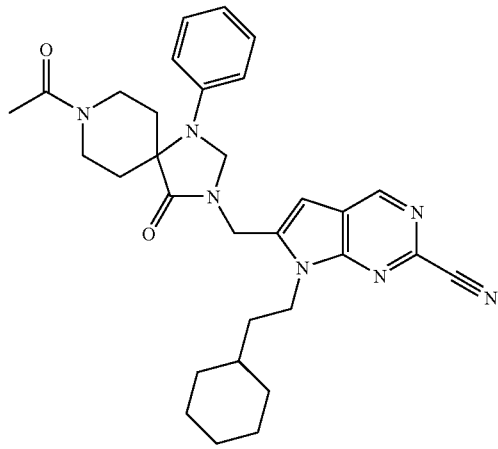

To a solution of 7-(2-cyclohexyl-ethyl)-6-(4-oxo-1-phenyl-1,3,8-triaza-spiro[4.5]dec-3-ylmethyl)-7H-pyrrolo[2,3-d]pyrimidine-2-carbonitrile trifluoroacetic acid salt (142 mg, 0.28 mol) in dichloromethane (2 ml), triethylamine (395 µl) and acetic anhydride (54 µl, 0.57 mmol) are added at 0° C. The reaction mixture is stirred for over night at room temperature, quenched with ice-water and extracted with ethyl acetate. The combined extracts are washed with H$_2$O, brine and dried over sodium sulphate. Chromatography on silica gel gives 90 mg of 6-(8-acetyl-4-oxo-1-phenyl-1,3,8-triaza-spiro[4.5]dec-3-ylmethyl)-7-(2-cyclohexyl-ethyl)-7H-pyrrolo[2,3-d]pyrimidine-2-carbonitrile in 58% yield.

Rf=0.30 (n-hexane:AcOEt=1:1). $^1$H-NMR (400 MHz, CDCl$_3$) δ: 0.97-1.40(m, 6H), 1.64-1.82(m, 9H), 2.14(s, 3H), 2.37-2.44(m, 2H), 3.40-3.48(m, 1H), 3.74-3.79(m, 1H), 3.93-4.01(m, 1H), 4.34-4.38(m, 2H), 4.56-4.66(m, 3H), 4.87(s, 2H), 6.61(s, 1H), 6.74-6.76(m, 2H), 6.91-6.95(m, 1H), 7.23-7.25(m, 2H), 8.94(s, 1H).

Example 4-16

6-(2-Acetyl-2,8-diaza-spiro[4.5]dec-8-ylmethyl)-7-(2-cyclohexyl-ethyl)-7H-pyrrolo[2,3d]pyrimidine-2-carbonitrile

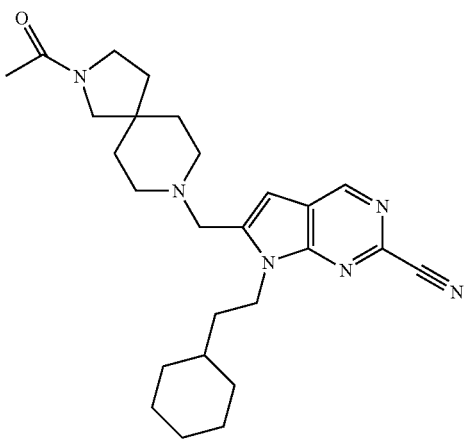

To a solution of 6-bromomethyl-7-(2-cyclohexyl-ethyl)-7H-pyrrolo[2,3-d]pyrimidine-2-carbonitrile (290 mg, 0.84 mmol) in DMF (1.7 ml), 2,8-Diaza-spiro[4.5]decane-2-carboxylic acid tert-butyl ester (201 mg, 0.84 mmol) and potassium carbonate (138 mg, 1.0 mmol) are added. The mixture is stirred at room temperature under nitrogen atomosphere for 14 h. The reaction mixture is diluted with water and extracted with AcOEt (twice). The combined organic layer is washed with water and brine, dried over MgSO$_4$, and concentrated in vacuo. The residue is purified by silica gel column chromatography (n-hexane:AcOEt=1:1) to give 8-[2-Cyano-7-(2-cyclohexyl-ethyl)-7H-pyrrolo[2,3-d]pyrimidin-6-ylmethyl]-2,8-diaza-spiro[4.5]decane-2-carboxylic acid tert-butyl ester in 71% yield. Rf=0.45(n-hexane:AcOEt=1:1).

To a solution of 8-[2-cyano-7-(2-cyclohexyl-ethyl)-7H-pyrrolo[2,3-d]pyrimidin-6-ylmethyl]-2,8-diaza-spiro[4.5]decane-2-carboxylic acid tert-butyl ester (300 mg, 0.59 mmol) in dichloromethane (5 ml), trifluoroacetic acid (3 ml) is added. After stirring for 1.5 h at room temperature, solvent is evaporated down to give 7-(2-cyclohexyl-ethyl)-6-(2,8-diaza-spiro[4.5]dec-8-ylmethyl)-7H-pyrrolo[2,3-d]pyrimidine-2-carbonitrile trifluoroacetic acid salt in quant yield.

Rf=0.10(CH$_2$Cl$_2$:MeOH=10:1)

To a solution of 7-(2-cyclohexyl-ethyl)-6-(2,8-diaza-spiro[4.5]dec-8-ylmethyl)-7H-pyrrolo[2,3-d]pyrimidine-2-carbonitrile trifluoroacetic acid salt in pyridine (5 ml), acetic anhydride (0.28 ml, 2.90 mmol) are added at 0° C. The reaction mixture is stirred for over night at room temperature, quenched with ice-water and extracted with ethyl acetate. The combined extracts are washed with H$_2$O, brine and dried over sodium sulphate. Chromatography on silica gel gives 79 mg of 6-(2-acetyl-2,8-diaza-spiro[4.5]dec-8-ylmethyl)-7-(2-cyclohexyl-ethyl)-7H-pyrrolo[2,3]pyrimidine-2-carbonitrile in 30% yield (3 steps).

Rf=0.30 (n-hexane:AcOEt=1:1). $^1$H-NMR (400 MHz, CDCl$_3$) δ: 1.00-1.84(m, 17H), 2.04(s, 3H), 2.33-2.56(m, 4H), 3.25-3.35(m, 2H), 3.47-3.53(m, 2H), 3.66-3.69(m, 2H), 4.38-4.43(m, 2H), 6.49(s, 1H), 8.87(s, 1H).

The invention claimed is:

1. A compound of formula I, or a pharmaceutically acceptable salt thereof:

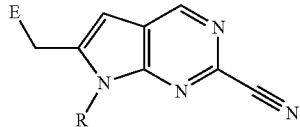

formula I wherein E is a radical of formula b

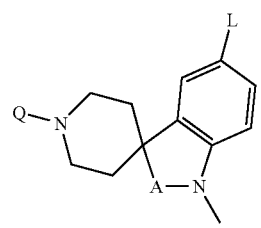

formula b wherein
- A is CH$_2$, CH$_2$—CH$_2$ or C=O;
- L is H, OCH$_3$, halo, or lower alkoxy;
- Q is H, lower alkyl, hydroxy substituted lower alkyl, optionally substituted aryl lower alkyl, lower alkyl sulfonyl, carbocyclic aryl lower alkyl, lower alkoxy-substituted carbocyclic aryl lower alkyl, halo-substituted carbocyclic aryl lower alkyl, N-heterocyclyl-substituted lower alkyl, lower alkoxy substituted carbocyclic aryl, amino carbonyl, cycloalkyl amino carbonyl, N-heterocyclyl substituted lower alkyl carbonyl, halo-substituted carbocyclic aryl lower alkyl, lower alkoxy carbonyl, or lower alkyl carbonyl; and
- R is lower alkyl, para-chlorophenylethyl, cyclohexylethyl, dimethylbutyl, difluorocyclohexylethyl, cyclopentylethyl or cycloheptylethyl.

2. A compound of formula I-(ii) or a pharmaceutically acceptable salt thereof

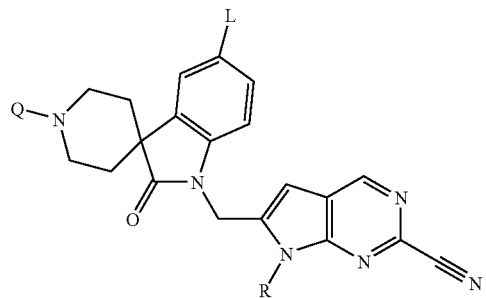

formula I-(ii)

wherein
- Q is H, lower alkyl, N-heterocyclyl substituted lower alkyl, halo substituted carbocyclic aryl lower alkyl, lower alkyl carbonyl; and
- L is H, OCH$_3$, halo, or lower alkoxy; and
- R is lower alkyl, para-chlorophenylethyl, cyclohexylethyl, dimethylbutyl, difluorocyclohexylethyl, cyclopentylethyl or cycloheptylethyl.

3. A compound of claim 1 wherein R is lower alkyl.

4. A compound of claim 1 wherein R is para-chlorophenylethyl, cyclohexylethyl, dimethylbutyl, difluorocyclohexylethyl, cyclopentylethyl or cycloheptylethyl.

5. A compound of claim 1 wherein R is 2,2-dimethylpropyl.

6. A compound of claim 1 wherein R is 3,3-dimethyl-butyl.

7. A compound of formula I-(iv) or a pharmaceutically acceptable salt thereof

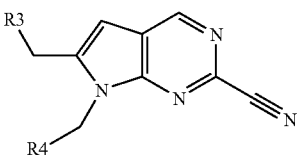

formula I-(iv)

wherein
R3 is

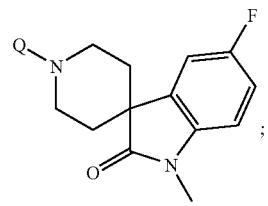

R4 is para-chlorophenylmethyl, cyclohexylmethyl, dimethylpropyl, difluorocyclohexylmethyl, cyclopentylmethyl or cycloheptylmethyl; and Q is H, lower alkyl, hydroxy substituted lower alkyl, optionally substituted aryl lower alkyl, lower alkyl sulfonyl, carbocyclic aryl lower alkyl, lower alkoxy-substituted carbocyclic aryl lower alkyl, halo-substituted carbocyclic aryl lower alkyl, N-heterocyclyl-substituted lower alkyl, lower alkoxy substituted carbocyclic aryl, amino carbonyl, cycloalkyl amino carbonyl, N-heterocyclyl substituted lower alkyl carbonyl, halo-substituted carbocyclic aryl lower alkyl, lower alkoxy carbonyl, or lower alkyl carbonyl.

8. A pharmaceutical composition comprising a compound according to claim 1 and a pharmaceutically acceptable diluent, excipient or carrier.

* * * * *